United States Patent
Han et al.

(10) Patent No.: US 7,943,131 B2
(45) Date of Patent: May 17, 2011

(54) METHODS FOR PROTECTING AND REGENERATING BONE MARROW USING CXCR3 AGONISTS AND ANTAGONISTS

(75) Inventors: Wei Han, Shanghai (CN); Huili Lu, Shanghai (CN); Di Xiang, Shanghai (CN)

(73) Assignee: General Regeneratives Holdings, Inc. (KY)

( * ) Notice: Subject to any disclaimer, the term of this patent is extended or adjusted under 35 U.S.C. 154(b) by 0 days.

(21) Appl. No.: 12/565,300

(22) Filed: Sep. 23, 2009

(65) Prior Publication Data
US 2010/0080756 A1  Apr. 1, 2010

Related U.S. Application Data

(60) Provisional application No. 61/100,347, filed on Sep. 26, 2008.

(51) Int. Cl.
| | |
|---|---|
| A61K 39/395 | (2006.01) |
| A61K 38/44 | (2006.01) |
| A61K 38/17 | (2006.01) |
| A61K 38/19 | (2006.01) |

(52) U.S. Cl. ............... 424/130.1; 424/143.1; 424/145.1; 424/158.1; 514/1.1

(58) Field of Classification Search .................. None
See application file for complete search history.

(56) References Cited

FOREIGN PATENT DOCUMENTS
WO    WO 03/024404    3/2003
WO    WO2008/116347    * 10/2008

OTHER PUBLICATIONS

Kouroumalis, The Journal of Immunology, 2005, vol. 175, pp. 5403-5411.*
Phillips, A., J Pharm Pharmacology, 2001, vol. 53, pp. 1169-1174.*
Pirollo et al. Cancer Res. 2008, vol. 68, No. 5, pp. 1247-1250.*
Vidal et al. European Journal of Cancer, 2005, vol. 41, pp. 2812-2818.*
U.S. Appl. No. 12/530,579, filed Mar. 26, 2007, Han et al.
Farber, J.M., "A macrophage mRNA selectively induced by γ-interferon encodes a member of the platelet factor 4 family of cytokines", *Proc. Natl. Acad. Sci. USA*, vol. 87, pp. 5238-5242, Jul. 1990.
Gasperini, S. et al., "Gene Expression and Production of the Monokine Induced by IFN-γ (MIG), IFN-Inducible T Cell α Chemoattractant (I-TAC), and IFN-γ-Inducible Protein-10 (IP-10) Chemokines by Human Neutrophils", *Journal of Immunology*, vol. 162, No. 8, pp. 4928-4937, Apr. 15, 1999.
Gorbachev, A.V. et al., "CXC Chemokine Ligand 9/Monokine Induced by IFN-γ Production by Tumor Cells is Critical for T Cell-Mediated Suppression of Cutaneous Tumors", *The Journal of Immunology*, vol. 178, No. 4, pp. 2278-2286, 2007.
Gosling, J. et al., "Molecular uncoupling of C-C chemokine receptor 5-induced chemotaxes and signal transduction from HIV-1 coreceptor activity", *Proc. Natl. Acad. Sci. USA*, vol. 94, pp. 5061-5066, May 1997.
Han, W. et al., "Local signals in stem cell-based bone marrow regeneration", *Cell Research*, vol. 16, pp. 189-195, 2006.
International Search Report and Written Opinion for International Application No. PCT/CN2007/000971 mailed Feb. 14, 2008.
Jinquan, T. et al., "CXC chemokine receptor 3 expression on CD34+ hematopoietic progenitors from human cord blood induced by granulocyte-macrophage colony-stimulating factor: chemotaxis and adhesion induced by its ligands, interferon γ-inducible protein 10 and monokine induced by interferon γ", *Blood Journal*, vol. 96, No. 4, pp. 1230-1238, Aug. 15, 2000.
Lazzeri, E. et al., "CXCR3-binding Chemokines: Novel Multifunctional Therapeutic Targets", *Current Drug Targets—Immune, Endocrine & Metabolic Disorders*, vol. 5, pp. 109-118, 2005.
Liao, F. et al., "Human Mig Chemokine: Biochemical and Functional Characterization", *J. Exp. Med.*, vol. 182, pp. 1301-1314, Nov. 1995.
Loos, T. et al., "TLR ligands and cytokines induce CXCR3 ligands in endothelial cells: enhanced CXCL9 in autoimmune arthritis", *Laboratory Investigation*, vol. 86, pp. 902-916, 2006.
Rollins, B.J., "Chemokines", *Blood Journal*, vol. 90, No. 3, pp. 909-928, 1997.
Ruehlmann, J. M. et al., MIG (CXCL9) Chemokine Gene Therapy Combines with Antibody-Cytokine Fusion Protein to Suppress Growth and Dissemination of Murine Colon Carcinoma:, *Cancer Research*, vol. 61, pp. 8498-8503, Dec. 1, 2001.
Yun, J.J. et al., "The Role of MIG/CXCL9 in Cardiac Allograft Vasculopathy", *American Journal of Pathology*, vol. 161, No. 4, Oct. 2002.
Zhang, R. et al., "Combination of MIG (CXCL9) chemokine gene therapy with low-dose cisplatin improves therapeutic efficacy against murine carcinoma", *Gene Therapy*, vol. 13, pp. 1263-1271, 2006.

* cited by examiner

*Primary Examiner* — Bridget E Bunner
*Assistant Examiner* — Fozia M Hamud
(74) *Attorney, Agent, or Firm* — Foley & Lardner LLP

(57) ABSTRACT

CXCR3 agonists, including natural CXCR3 ligands, promote bone marrow regeneration, increase peripheral white blood cells, and increase survival if administered prior to treatment of a subject with chemotherapy or radiotherapy. Similar effects are obtained by administering an CXCR3 antagonists following chemotherapy radiotherapy. Compositions and methods are presented for the treatment of cancer and bone marrow diseases.

5 Claims, 10 Drawing Sheets

METHODS FOR PROTECTING AND REGENERATING BONE MARROW USING CXCR3 AGONISTS AND ANTAGONISTS

CROSS-REFERENCE TO RELATED APPLICATIONS

This application claims priority to U.S. Provisional Patent Application No. 61/100,347, filed Sep. 26, 2008, the entire contents of which are hereby incorporated by reference in its entirety.

TECHNICAL FIELD

The present technology relates generally to methods of protecting a subject against the harmful effects of chemotherapy and radiotherapy. In particular, this technology relates to methods for promoting protection and regeneration of bone marrow using CXCR3 agonists and antagonists.

BACKGROUND

The following description is provided to assist the understanding of the reader. None of the information provided or references cited is admitted to be prior art to the present invention.

Hematopoiesis is a complex process in which hematopoietic stem cells are stimulated to differentiate into multiple lineages by various growth factors. It is assumed that the majority of hematopoietic stem cells are in the quiescent ($G_0$) phase of the cell cycle, and only a few actively cycling hematopoietic stem cells supply all the hematopoietic cells at a given time.

Myelosuppression is the most common adverse effect of cytotoxic chemotherapy and is a major limiting factor in the clinical treatment of cancer. Therefore, promotion of hematopoiesis remains an extremely important challenge in cancer therapy. A large number of cytokines have been screened for their chemoprotective potential. Administration of recombinant colony-stimulating factors, such as granulocyte-macrophage colony stimulating factor (GM-CSF), granulocyte colony stimulating factor (G-CSF), and stem cell factor (SCF), alleviates chemotherapy-induced myelotoxicity augmenting proliferation of hematopoietic progenitor cells in the bone marrow and accelerates the recovery of peripheral blood cells.

SUMMARY

The disclosure provides methods for using CXCR3 agonists and/or antagonists to protect hematopoietic cells and other bone marrow cells from the harmful effects of chemotherapy or radiotherapy. Without wishing to be limited by theory, the agonist protects hematopoietic cells from chemotherapy or radiation damage and preserves more hematopoietic cells, which aids in recovery from chemotherapy or radiation therapy. The antagonist reduces the inhibition of cycling of hematopoietic cells after chemotherapy or radiation damage, which allows the cells respond to the cytokine stimulation readily.

Thus, the methods have the ability to protect hematopoietic cells, particularly, stem cells and progenitor cells, from the destructive effects of chemotherapy, radiotherapy or a combination thereof. Administration of a CXCR3 agonist as an agent or therapeutic agent prior to administration of radiation therapy results in a more rapid recovery of bone marrow and circulating leukocytes as well as a higher survival rate in the animals. An anti-CXCL9, anti-CXCL10, and/or anti-CXCL11 antibody as an agent or therapeutic agent leads to better recovery of peripheral white cell counts and a higher survival rate following radiation therapy. CXCR3 agonists and antagonists can also be administered as compositions comprising pharmaceutically acceptable carriers. Moreover, CXCR3 agonists and antagonists may be administered as part of a therapeutic protocol that can provide treatment before and after chemotherapy or radiotherapy.

The disclsoure also provides treatment methods for cancer and various bone marrow disorders. On the one hand, the methods are based on the myelosuppressive action of CXCR3 agonists and, on the other hand, on the ability of CXCR3 antagonists to counteract such myelosuppressive effects. The disclsoure offers novel ways to enhance the recovery of the suppressed hematopoietic system as part of a regimen of chemotherapy or radiation therapy, particularly, in the treatment of cancer.

In one aspect, the disclosure provides a method for myeloprotection comprising administering an effective amount of a CXCR3 agonist to a subject prior to administering chemotherapy or radiotherapy to the subject, wherein following chemotherapy or radiotherapy the bone marrow cell density or the level of peripheral white blood cells of the subject is increased compared to a control subject not receiving the CXCR3 agonist.

In one embodiment, the chemotherapy is cell cycle specific. In another embodiment, the chemotherapy is cell cycle nonspecific. For example, the chemotherapy may comprise administering an agent selected from the group consisting 5-fluorouracil, Ara-C, vinblastine, methotrexate, cyclophosphamide, doxorubicin, cisplatin, and busulfan. In one embodiment, radiotherapy comprises administering external beam radiation or a radiopharmaceutical agent.

In one embodiment, the CXCR3 agonist is administered in daily doses for two or more days prior to administering the chemotherapy or the radiotherapy. In one embodiment, the CXCR3 agonist is administered for 5 days or more.

In one embodiment, the CXCR3 agonist is selected from the group consisting of: CXCL9, CXCL10, CXCL11, and combinations thereof. In one embodiment, the CXCR3 agonist is recombinant human CXCL9 or biologically active fragments or variants thereof. In one embodiment, the CXCR3 agonist is a conjugated form of CXCL9 or an albumin-CXCL9 fusion protein.

In one embodiment, the method further comprises administering an additional myelosuppressive agent to the subject prior to the chemotherapy or the radiotherapy. For example, the myelosuppressive agent may be CCL3 or IL-1Ra.

In one embodiment, the method further comprises administering a hemopoietic growth factor to the subject following the chemotherapy or the radiotherapy. For example, the growth factor may be one or more of GM-CSF, G-CSF, TPO, or IL-11. The cytokines can be GM-CSF and G-CSF which promote the recovery of granulocytes and TPO and/or IL-11 promote the recovery of platelets.

In one aspect, the disclosure provides a method for enhanced hemotopoietic recovery following chemotherapy or radiotherapy, the method comprising: administering to the subject after chemotherapy or radiotherapy an effective amount of a CXCR3 antagonist, wherein following chemotherapy or radiotherapy the bone marrow cell density or the level of peripheral white blood cells of the subject is increased compared to a control subject not receiving the CXCR3 antagonist.

In one embodiment, the CXCR3 antagonist is selected from the group consisting of: an anti-CXCL9 antibody, an anti-CXCL10 antibody, an anti-CXCL11 antibody, a CXCR3 antibody, and combinations thereof.

In one embodiment, the CXCR3 antagonist is administered in daily doses for two or more days following the administration of the chemotherapy or the radiotherapy.

In one aspect, the disclosure provides a method of preventing bone marrow cell damage during chemotherapy or radiotherapy. The method includes administering an effective amount (e.g., therapeutically effective amount) of CXCR3 agonists, e.g., CXCL9, CXCL10, and/or CXCL11, to a subject before the subject receives chemotherapy or radiotherapy. After chemotherapy or radiation therapy, the bone marrow cell density of the subject is increased compared to a subject that does not receive CXCL9, CXCL10, and/or CXCL11. That is, the reduction of bone marrow cell density that normally follows chemotherapy or radiation therapy is partially or entirely reversed by pretreatment with a CXCR3 agonist. The bone marrow cell density may be increased at least 5%, at least 10%, at least 20%, at least 30%, at least 40%, or at least 60% compared to a subject that does not receive CXCL9, CXCL10, and/or CXCL11.

Another aspect is a method of increasing the level of peripheral white blood cells following chemotherapy or radiotherapy. The method comprises administering an effective amount of CXCL9, CXCL10, and/or CXCL11 to a subject prior to administering chemotherapy or radiotherapy to the subject. The reduction of peripheral leukocytes that normally follows chemotherapy or radiation therapy is partially or entirely reversed by pretreatment with CXCL9, CXCL10, and/or CXCL11.

A further aspect is a method of treating cancer. According to this method, CXCL9, CXCL10, and/or CXCL11 is administered to a subject with cancer and then chemotherapy or radiation therapy is administered to the subject.

In another aspect, a method of enhancing bone marrow recovery after chemotherapy or radiotherapy is provided. The method comprises administering to the subject an effective amount of an agent (e.g., therapeutic agent) selected from an anti-CXCL9 antibody, an anti-CXCL10 antibody, an anti-CXCL11 antibody, a CXCL9 siRNA, a CXCL10 siRNA, a CXCL11 siRNA, a CXCL9 antisense nucleic acid, a CXCL10 antisense nucleic acid, a CXCL11 nucleic acid, a CXCR3 antibody, a CXCR3 siRNA, a CXCR3 antisense nucleic acid and a CXCR3 antagonist, as well as combinations thereof. Typically, following chemotherapy or radiotherapy, the bone marrow cell density of the subject is increased compared to a control subject not receiving the agent. An agent or therapeutic agent can also be administered as a composition comprising a therapeutically effective amount of the agent and a pharmaceutically acceptable carrier.

In another aspect, a CXCR3 agonist can be administered via a eukaryotic expression vector. An exemplary expression vector for a method of the invention is pcDNA3. 1(–). An expression vector can be administered by electroporation of skeletal muscle. Alternatively, an expression vector can be administered in vitro to bone marrow cells from the subject. In one aspect, a method can comprise administering a CXCR3 agonist in a conjugated form or a CXCR3 agonist fusion protein. An exemplary CXCR3 agonist fusion protein can be an albumin-CXCL9 fusion protein. Albumin can be a serum albumin or a human serum albumin (HSA). The disclosure contemplates that a conjugated form of a CXCR3 agonist or a CXCR3 agonist fusion protein can alter the half-life (e.g., therapeutic half-life) of a CXCR3 agonist, which could be advantageous for certain chemotherapy or radiotherapy treatment protocols.

In one aspect, a method can comprise administering a CXCR3 antagonist selected from an anti-CXCL9 antibody, an anti-CXCL10 antibody, an anti-CXCL11 antibody, a CXCL9 siRNA, a CXCL10 siRNA, a CXCL11 siRNA, a CXCL9 antisense nucleic acid, a CXCL10 antisense nucleic acid, a CXCL11 nucleic acid, a CXCR3 antibody, a CXCR3 siRNA, a CXCR3 antisense nucleic acid and a CXCR3 small molecule antagonist, as well as combinations thereof. For example, the agent can be administered in daily doses for, but not limited to, two or more days following the administration of chemotherapy or said radiotherapy. In suitable embodiments, the agent can be administered for at least 10 days following the administration of chemotherapy or radiotherapy. In another aspect, an anti-CXCL9 antibody, an anti-CXCL10 antibody, an anti-CXCL11 antibody, or anti-CXCR3 antibody can be a polyclonal antibody or a monoclonal antibody. The antibody can also be a Fab fragment, a scFv antibody or a single domain antibody. The antibody can also be a chimeric antibody, a humanized antibody (optionally including back mutations) or a human antibody. An antibody can also be provided as a conjugated form.

In one aspect, a method comprises administering CXCL9, CXCL10, and/or CXCL11 siRNA. For example, CXCL9 siRNA can comprise a sequence complementary to 18 to 30 consecutive nucleotides of the CXCL9 mRNA.

In some embodiments, a bone marrow disorder to be treated is selected from the group consisting of pancytopenia, aplastic anemia, thrombocytopenia, leucopenia, neutropenia, and myelofibrosis. The agent can be administered in daily doses for, but not limited to, two or more days. Similarly, the method can comprise administering the agent for at least 10 days.

Any of the methods can comprise a subject that is a mammal, such as a human. In another aspect, a method of enhancing the effectiveness of chemotherapy or radiotherapy to treat cancer is provided. The method may comprise administering to a subject with cancer an effective amount of a CXCR3 agonist and administering chemotherapy or radiotherapy at a higher dose than would be administered in the absence of the administration of a CXCR3 agonist. In such methods, the effectiveness of the chemotherapy or radiotherapy can be enhanced by administering a CXCR3 agonist to a subject.

DETAILED DESCRIPTION

Figure 1A:
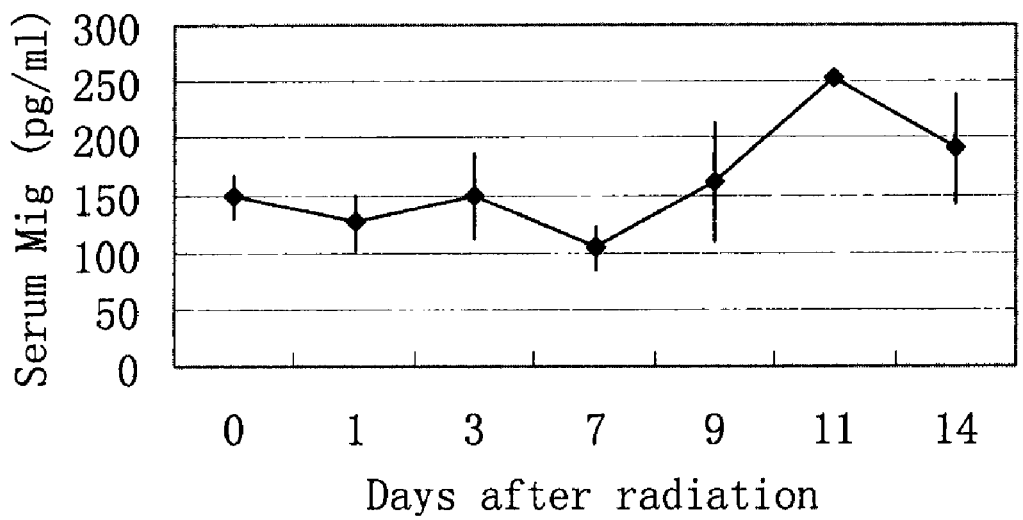
FIG. 1 shows graphs of the serum level of CXCR3 ligands CXCL9 (FIG. 1A), CXCL10 (FIG. 1B), and CXCL11 (FIG. 1C) after radiation treatment in mice.

The present technology generally relates to methods of preventing myelotoxicity associated with chemotherapy and radiotherapy. In particular, the methods comprise administration of a CXCR3 agonist (e.g. a CXCR3 ligand such as CXCL9, CXCL10, CXCL11) to promote bone marrow regeneration, increase peripheral white blood cells, increase platelet level, and enhance survival of subjects, if administered prior to treatment with radiotherapy or a chemotherapeutic agent. The methods also relate to administration of a CXCR3 antagonist (e.g., an antibody, antisense nucleic acid, or siRNA directed to CXCL9, CXCL10, CXCL11, and/or CXCR3) to promote bone marrow regeneration, increase peripheral white blood cells, increase platelet level, and enhance survival of subjects, if administered after treatment with radiotherapy or a chemotherapeutic agent. Compositions and methods are presented for the treatment of cancer.

In the description that follows, a number of terms are utilized extensively. Definitions are herein provided to facilitate understanding of the invention. The terms described below are more fully defined by reference to the specification as a whole. Units, prefixes, and symbols may be denoted in their accepted SI form. Unless otherwise indicated, nucleic acids are written left to right in 5' to 3' orientation; amino acid sequences are written left to right in amino to carboxy orientation. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes.

The terms "a" and "an" as used herein mean "one or more" unless the singular is expressly specified.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid.

The term "bone marrow cells" generally refers to cells that reside in and/or home to the bone marrow compartment of a mammal. Included in the term "bone marrow cells" is not only cells of hematopoietic origin, including but not limited to hematopoietic repopulating cells, hematopoietic stem cell and/or progenitor cells, but any cells that may be derived from bone marrow, such as endothelial cells, mesenchymal cells, bone cells, neural cells, and supporting cells (stromal cells).

The term "chemotherapy" refers to any therapy that includes natural or synthetic chemotherapeutic agents now known or to be developed in the medical arts. Examples of chemotherapeutic agents include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include chemotherapy with docetaxel, cisplatin, 5-fluorouracil, fludarabine, cyclophosphamide, and bendamustine.

As used herein, "CXCR3 agonist" refers to any substance which binds to and activates CXCR3, including natural ligands for CXCR3 as well as fragments, mutants, and modifications of a naturally occurring ligand. CXCR3 ligands include, but are not limited to, human CXCL9, CXCL10, and CXCL11 polypeptides. Exemplary agonists of CXCR3 are generally described in U.S. Pat. No. 6,184,358, International Publication No. WO 2005/113597, WO 2004/083394 and U.S. Publication No. 2005/0119174. The term CXCR3 agonist also refers to an agent (e.g., a small molecule) that upregulates (e.g., potentiates or supplements) a CXCR3 signaling pathway. A CXCR3 agonist can also be a compound which increases the interaction of a CXCR3 receptor with another molecule, e.g., a CXCR3 ligand.

The term "CXCR3 antagonist" includes substances that block or inhibit the activity of CXCR3 signaling pathway, either acting alone or in the presence of a natural ligand or agonist of CXCR3, and also includes substances that bind to a natural ligand of CXCR3 and prevent it from binding to CXCR3 or activating CXCR3. CXCR3 antagonists can be neutral antagonists, for example, which block the activity of CXCR3 signaling by inhibiting the binding of physiological ligands to CXCR3, or inverse agonists, which shift the equilibrium of the active form and inactive form of CXCR3 toward the more inactive form. CXCR3 antagonists include substances that bind to CXCR3 but do not promote the activity of CXCR3 signaling in a cell. CXCR3 antagonists encompass both known and novel compounds that possess any one of the above-described properties.

As used herein, "CXCL9", "CXCL10", and "CXCL11" refers to any mammalian CXCL9, CXCL10, or CXCL11 polypeptide, respectively, including fragments, mutants, and modifications of a naturally occurring polypeptide, which binds to and activates CXCR3, and includes mature as well as full-length forms. Modifications of a naturally occurring CXCL9 include conservative amino acid substitutions, insertions, deletions, or truncations resulting in a polypeptide that binds CXCR3 and elicits a CXCR3-mediated response in a target cell.

As used herein, the term "effective amount" or "pharmaceutically effective amount" or "therapeutically effective amount" or "prophylactically effective amount" of a composition, is a quantity sufficient to achieve a desired therapeutic and/or prophylactic effect. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. In some embodiments, an effective amount of a CXCR3 agonist composition may be administered to a subject prior to administration of a chemotherapeutic agent or radiation therapy. An effective amount of CXCR3 agonist may include an amount in which the myelosuppressive effects of chemotherapy or radiation therapy are ameliorated. In some embodiments, an effective amount of a CXCR3 antagonist composition may be administered after administration of a chemotherapeutic agent or radiation therapy. An effective amount of CXCR3 antagonist may include an amount in which the myelosuppressive effects of chemotherapy or radiation therapy are ameliorated.

As used herein, "expression" includes, but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

The term "hematopoietic cells" refers to morphologically recognizable and functionally capable cells circulating in blood, including mature hematopoietic cells and hematopoietic stem and progenitor cells. Mature hematopoietic cells include erythrocytes, macrophages or monocytes, neutrophilic, eosinophilic, and basophilic granulocytes, B-, T, non B-, non T-lymphocytes, and platelets. These mature hematopoietic cells derive from and are replaced, on demand, by morphologically recognizable dividing precursor cells for the respective lineages such as erythroblasts for the erythrocyte series, myeloblasts, promyelocytes and myelocytes for the monotyte/macrophage and granulocyte series, and megakaryocytes for the platelets.

The precursor cells derive from more primitive cells that can simplistically be divided into two major subgroups: stem cells and progenitor cells. The definitions of stem and progenitor cells are operational and depend on functional, rather than on morphological criteria. Stem cells have extensive self-renewal or self-maintenance capacity, a necessity since an absence or depletion of these cells could result in the complete depletion of one or more cell lineages or cell types, events that would lead within a short time to disease and death. Some of the stem cells differentiate upon need, but some stem cells or their daughter cells produce other stem cells to maintain the pool of these cells. Thus, in addition to maintaining their own kind, pluripotential stem cells, or hematopoietic repopulating cells, are capable of differentiation into several sub-lines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, L. G., 1979, *Blood Cells* 5: 447).

The term "interleukin-1 receptor antagonist" or "IL-1Ra" refers to a 17-kDa polypeptide that is produced by several cell types in mammals, including adherent monocytes. IL-1Ra is a human protein that acts as an inhibitor of interleukin-1 activity and is a member of the IL-1 family, which also includes IL-1α and IL-1β. A non-exclusive, non-limiting, non-exhaustive list of IL-1 receptor antagonists includes intracellular IL-1Ra (icIL-1Ra), IL-1Raβ (see, e.g., PCT Publication No. WO 99/36541), IL-1Ra variants, and IL-1Ra derivatives. Certain IL-1Ra receptor antagonists, including IL-1Ra and variants and derivatives thereof, as well as methods of making and using them, are described, e.g., in U.S. Pat. Nos. 5,075,222; 6,599,873 B1; 5,863,769; 5,858,355; 5,739,282; 5,922,573; 6,054,559; WO 91/08285; WO 91/17184; WO 91/17249; AU 9173636; WO 92/16221; WO 93/21946; WO 94/06457; WO 94/21275; FR 2706772; WO 94/21235; DE 4219626, WO 94/20517; WO 96/22793; WO 96/12022; WO 97/28828; WO 99/36541; WO 99/51744. An IL-1 receptor antagonist may be glycosylated or non-glycosylated.

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters or by manual alignment and visual inspection (see, e.g., NCBI web site). Such sequences are then said to be "substantially identical." The term also includes sequences that have deletions and/or additions, as well as those that have substitutions. As described below, the algorithms can account for gaps and the like. Typically, identity exists over a region that is at least about 25 amino acids or nucleotides in length, or over a region that is at least about 50-100 amino acids or nucleotides in length.

An "isolated" or "purified" polypeptide or biologically-active portion thereof is substantially free of cellular material or other contaminating polypeptides from the cell or tissue source from which a polypeptide, e.g., the CXCR3 agonist polypeptide, is derived, or substantially free from chemical precursors or other chemicals when chemically synthesized. For example, an isolated CXCR3 agonist polypeptide would be free of materials that would interfere with therapeutic uses of the agent. Such interfering materials may include enzymes, hormones and other proteinaceous and nonproteinaceous solutes.

The term "myeloprotective effect" refers to the effect that substantially arises from the administration of the compositions to a subject prior to the administration of a chemotherapeutic agent. This protective effect can be manifested in a subject as an increased bone marrow cell density, increased level of platelets, and/or increased level peripheral white blood cells compared to a subject not receiving the compositions prior to receiving the chemotherapeutic agent.

The terms "myelotoxicity" or "hematopoietic toxicity" refer to a toxicity that substantially arises from the administration of a treatment to a subject that adversely affects the hematopoietic system of the subject. This adverse effect can be manifested in the subject broadly whereby many hematopoietic cell types are altered from what is considered to be normal levels, as a result of the treatment, or as a result of the treatment and the disease state combined, or the adverse effect can be manifested in the subject more specifically whereby only one or a few hematopoietic cell types are altered from what is considered to be normal levels, as a result of the treatment, or as a result of the treatment and the disease state combined.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. In a particular embodiment, the polynucleotide contains polynucleotide sequences encoding a CXCR3 agonist (e.g., mammalian CXCL9, CXCL10, or CXCL11), IL-1Ra, or a biologically active fragment or variant thereof.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the term "subject" refers to an organism administered one or more compositions of the invention. Typically, the subject is a mammal, such as an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like). In a particular embodiment, the subject is a human.

As used herein, the term "substitution" is one of mutations that is generally used in the art. Those substitution variants have at least one amino acid residue in the polypeptide molecule replaced by a different residue. "Conservative substitutions" typically provide similar biological activity as the unmodified polypeptide sequence from which the conservatively modified variant was derived. Conservative substitutions typically include the substitution of one amino acid for another with similar characteristics. Conservative substitution tables providing functionally similar amino acids are well known in the art. For example, the following six groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic (Cationic): Arginine (R), Lysine (K), Histidine (H); Acidic (Anionic): Aspartic acid (D), Glutamic acid (E); Amide: Asparagine (N), Glutamine (Q).

As used herein, the terms "treating" or "treatment" or "alleviation" refers to both therapeutic treatment and prophylactic or preventative measures, wherein the object is to prevent or slow down (lessen) the targeted pathologic condition or disorder.

Methods for Myeloprotection and Enhanced Hematopoietic Recovery

The present technology relates to therapeutic methods for treating diseases and disorders in which increased amounts of hematopoietic cells are desirable (e.g., conditions where the recommended therapy has associated myelotoxicities, thus leading to reduced numbers of one or more hematopoietic cell types or lineages) by administration of a CXCR3 agonist or antagonist, or biologically active fragments or variants thereof. Thus, embodiments of the invention provide methods of alleviating or treating various hematopoietic cell deficiencies, including deficiencies in hematopoietic repopulating cells, progenitor and stem cells, by the direct administration of a CXCR3 agonist or antagonist to a subject.

In one aspect, this technology relates to novel properties of the chemokines CXCL9, CXCL10, and CXCL11. CXCR3 agonists, including CXCL9, CXCL10, and CXCL11, surprisingly play a central role in the regeneration of bone marrow after injury. The inventors have discovered novel compositions and methods involving CXCR3 agonists that are useful for preventing the loss of bone marrow cells in response to damaging environmental factors, including chemotherapeutic agents and radiation, on the one hand, and useful for regenerating already damaged bone marrow on the other. The compositions and methods of the invention can be used to reduce the serious, sometimes fatal loss of bone marrow function associated with chemotherapy or radiation therapy and are especially useful as an adjunct therapy in the treatment of cancer. They also can be used to remedy the loss of bone marrow cells associated with bone marrow disorders such as aplastic anemia and leukemia.

CXCR3 agonists (e.g., CXCL9, CXCL10, and CXCL11) have potent antimyelogenic effects, limiting the proliferation of bone marrow progenitor cells and resulting in a reduction in bone marrow cell number. Without intending to limit the invention to any particular mechanism, it appears that this antimyelogenic property leads to the protective effect of CXCR3 agonists on bone marrow cells that are subsequently challenged with damaging agents such as chemotherapeutic drugs or radiation. By inducing a quiescent, nonproliferating state, CXCR3 agonist administration prevents destruction of critical progenitor cells or stem cells in bone marrow during chemotherapy or radiotherapy, resulting in vastly improved recovery subsequent to such therapy. This effect can be utilized by the physician to either improve the safety and tolerability of chemotherapy or radiation therapy, or to increase the therapeutic efficacy by raising the dose of the chemotherapeutic agent or radiation to level that would not be tolerated without CXCR3 ligand treatment. Therefore, through the use of the invention, the safety and effectiveness of common cancer therapies can be enhanced.

Furthermore, the inventors have discovered that effectors of CXCR3 continue to play a role subsequent to bone marrow injury. The present inventors unexpectedly found that CXCL9, CXCL10, and CXCL11 gene expression in bone marrow increases dramatically after treatment with radiation. Thus, during the critical recovery period, the antiproliferative activity of CXCR3 ligands become stronger, serving as an impediment to bone marrow recovery. Therefore, the administration of an antagonist of a CXCR3 activity during the period following chemotherapy or radiation therapy will lead to improved recovery of bone marrow cells (i.e., faster increase in cell number, and/or higher eventual cell number). Again, without limiting the invention to any particular mechanism, the administration of any agent that antagonizes the activity of a CXCR3 appears to reduce the harmful effect caused by the increase in CXCR3 ligand expression after exposure to a bone marrow damaging agent.

One embodiment is a method for preventing bone marrow cell damage resulting from chemotherapy or radiotherapy, or exposure to myelotoxic agent. The method includes administering an effective amount of a CXCR3 agonist to a subject who is about to receive either chemotherapy or radiation therapy. The outcome of performing this method is that the cell density, or total cell number per unit volume of bone marrow, is greater after chemotherapy or radiotherapy than if the method had not been performed. Various types of damage to bone marrow can be prevented by this method. Chemotherapeutic agents as well as radiation cause damage to DNA of cells in the bone marrow, and if that damage is severe enough, apoptosis is induced and the cell dies. This is the underlying mechanism of cancer treatment with these therapies. However, damage leading to apoptosis of any of a variety of bone marrow progenitor cells or stem cells will reduce the number of bone marrow cells and the number of circulating leukocytes, as well as weaken the entire immune system, within a few days after the chemical agent or radiation is administered. Thus, administering a CXCR3 agonist (e.g., CXCL9, CXCL10, or CXCL11) prior to chemotherapy or radiotherapy preserves stem cells and progenitor cells by reducing the damaging effects on these cells, resulting in quicker recovery of bone marrow and immune function after the treatment, and improving the selectivity of chemotherapy or radiation therapy for cancer cells compared to normal cells.

CXCR3 agonists (e.g., CXCR3 ligands CXCL9, CXCL10, and CXCL11) promote bone marrow regeneration, increase peripheral white blood cells, and increase survival if administered prior to treatment of a subject with chemotherapy or radiation therapy. Similar effects are obtained by administering a CXCR3 antagonist following chemotherapy or radiation therapy. Compositions and methods are presented for the treatment of cancer and bone marrow diseases.

Examples of CXCR3 antagonists include degradation products of physiological ligands for CXCR3 such as CXCL10 (IP10), CXCL9 (Mig), CXCL11 (I-TAC), and BCA-1; certain kinds of CC chemokines that possess affinity for CXCR3, such as eotaxin (*J. Biol. Chem.*, 273(29): 8288-18291 (1998)). Further exemplary antagonists of CXCR3, including small molecules, are generally described in International Publication Nos. WO 2006/088920, WO 2006/088837, WO 2006/091428, WO 2006/088921, WO 2006/088919, WO 2006/088836, WO 2007/002742, WO 2007/002701, WO 2006/137934, WO 2006/129679, WO 2005/113597, WO 2002/085861, U.S. Publication Nos. 2006/0240437, 2006/0204498, 2006/0276480, 2006/0276479, 2006/0276448, 2006/0276457, 2006/0217392, 2007/002 1611, 2007/00 1 5 7 73, 2005/0 119174, 2004/0242498, 2003/0077247, 2002/0018776, 102002/0169159 and European Publication Nos. EP 1603896, EP 1723970.

The amino acid sequences of CXCL9, CXCL10, and CXCL11, which are physiological ligands for CXCR3, and the nucleotide sequences of their genes are known. For example, the human cDNA sequences of these ligands have been registered with GenBank under accession numbers NM 001565, NM 002416, NM 005409, and NM 006419, respectively, CXCL9, CXCL10, and CXCL11 encompass, in addition to the corresponding naturally occurring chemokine proteins derived from humans and other mammals, recombinant proteins produced from recombinant cells containing DNAs that encode them.

CXCR3 agonists or antagonists can also be used in the form of a prodrug that is metabolized in the body of a recipient animal and results in a substance that exhibits the respective agonist or antagonist activity with respect to CXCR3. When the CXCR3 agonist or antagonist is a peptide substance such as CXCL9, CXCL10, and CXCL11, "prodrugs" thereof also encompass an expression vector containing a nucleic acid sequence that encodes the peptide, and a host cell transfected with such an expression vector. In the expression vector, a DNA that encodes a physiological ligand possessing agonist or antagonist activity against CXCR3, such as CXCL9, CXCL10, and CXCL11, or a modification thereof, is operably linked to a promoter capable of exhibiting promoter activity in the cells of the recipient mammal.

Administration of a CXCR3 agonist refers to administering a CXCR3 agonist polypeptide, e.g., a CXCL9, CXCL10, or CXCL11 polypeptide, including sequence variants such as insertions, deletions, and conservative amino acid substitutions, or related forms such as mutations or polypeptides of related species having a high degree of sequence similarity. In general, a CXCR3 agonist for administration is one which is functionally active as determined by its antimyelogenic effect, or as determined by its ability to prevent loss of bone marrow cells following chemotherapy or radiation therapy that causes a significant loss of bone marrow cells within a few days after administration. A CXCR3 agonist for administration is suitably a CXCR3 agonist having the same amino acid sequence as the CXCR3 agonist of the species to which it is administered, so as to avoid any immune response against the administered CXCR3 agonist. For example, if the subject is human, then the administered CXCL9 is preferably human CXCL9, e.g., recombinant human CXCL9 (rHuCXCL9). Alternatively, a CXCL9 having a different but closely related amino acid sequence can be administered, for example an amino acid sequence which is at least 70%, 90%, 95%, 97%, 98%, or 99% identical according to a sequence alignment performed using a BLAST algorithm.

Additionally, in certain embodiments, one skilled in the art can review structure-function studies and identify residues in similar polypeptides that are important for activity or structure. In view of such a comparison, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can analyze the three-dimensional structure and amino acid sequence in relation to known structures in similar polypeptides. Moreover, in certain embodiments, one skilled in the art may generate test variants containing a single amino acid substitution at each desired amino acid residue. In certain embodiments, the variants can then be screened using activity assays known to those skilled in the art. Such variants could be used to gather information about suitable variants. For example, in certain embodiments, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

Yet another form of administering a CXCR3 agonist is a eukaryotic expression vector that encodes and expresses the CXCR3 agonist of the subject's species. Such an expression vector can produce a transiently heightened expression level for the CXCR3 agonist over the desired time window, e.g., for several days prior to administering the chemotherapy or radiotherapy. Such vectors can also be targeted if desired. For example, one method is to perform ex vivo transfection of bone marrow cells using such a vector, and then to return the cells to the patient, e.g., by intravenous injection.

The administration of a CXCR3 agonist should precede a chemotherapeutic or radiotherapeutic intervention in order to have a beneficial effect. In some embodiments, a CXCR3 agonist is administered for 2 or more days prior to the bone marrow damaging treatment. In some embodiments, the CXCR3 agonist is administered for at least 3, at least 5, at least 7, or at least 10 days prior to treatment. Administration can be, for example, by one or more doses per day during the window of time immediately preceding treatment. An additional dose can be administered on the same day as chemotherapy or radiotherapy treatment, or alternatively the final administration can take place one day, two days, or three days or more before the treatment. Long-lasting conjugates, or albumin fusion proteins, of a CXCR3 agonist also may be administered to improve the effectiveness or reduce the number of doses required. Administration can be by any suitable means. For polypeptides, a suitable means of administration is by intravenous injection; however, other routes can be used as well, including topical formulations, nasal sprays, pills, tablets, caplets, or suppositories. Generally, the administration of a CXCR3 agonist will terminate when the chemotherapy or radiotherapy is given to the subject; continued administration after such therapy can be harmful, because it can extend the impact on bone marrow cells and impede recovery.

The subject who receives the CXCR3 agonist therapy is generally one who is scheduled for either chemotherapy or radiotherapy, or can also be a person who is about to be exposed to, or who is at risk for exposure to, a significant amount of bone marrow damaging radiation or chemicals. For example, the subject can be a human patient or an animal who has been diagnosed with a cancer for which chemotherapy or radiation therapy is considered to be an advantageous treatment. Most types of cancer can be treated with either chemotherapy or radiation therapy. A variety of animal models for such cancers are known, which can be used to explore the effectiveness of various agents of the invention, as well as administration and dosing protocols. The subject could also be a person who is about to enter an area characterized by high radiation exposure or chemical exposure, such as associated with space flight or clean-up activities resulting from a radiation spill, nuclear accident, an explosive device or a chemical spill.

The administration of an effective amount of CXCR3 agonist is accompanied by an improvement of bone marrow condition following the chemotherapy, radiotherapy, or other damaging agent exposure. Bone marrow condition for a subject has improved if one or more of the following occurs: the density of bone marrow cells is greater than if no administration of CXCR3 agonist was made; the density of progenitor cells or stem cells in bone marrow is greater than if no administration was made; the mass of bone marrow tissue is greater than if no administration was made; or the rate of bone marrow cell proliferation is greater than if no administration was made. The determination of effectiveness can be made at any time following therapy with a chemical or radiation agent. For example, the determination of effectiveness can be made at 1, 2, 3, 4, 5, 6, 7, 8, 9, 10 or more days after the agent (e.g., chemotherapeutic agent) is delivered to the subject. A bone marrow sample can be obtained from any portion of bone marrow in the subject's body for this analysis. In order to compare the result to the expected result if no administration was made, data can be collected from one or more control individuals, typically from several individuals, who receive the same or similar chemotherapy or radiation therapy, but who do not receive a CXCR3 agonist. In one embodiment, the control population is being treated for the same condition, e.g., for the same type of cancer. An amount is an effective amount (e.g., therapeutically effective amount) if any benefit whatsoever is produced compared to the control population. For example, if the treated individual or group has a bone marrow condition parameter, (e.g., proliferation rate of a given progenitor cell type) whose value, or mean value, is closer to the normal value (e.g., higher than) the value or mean value from a control individual or control group, then the bone marrow condition of the treated individual or group is improved. Statistical methods optionally can be applied to this analysis as appropriate. In different embodiments, an effective amount can be an amount that improves bone marrow condition by at least 5%, at least 10%, at least 15%, at least 20%, at least 25%, at least 30%, at least 40%, at least 50% or more.

Another embodiment involves the administration of a CXCR3 agonist as described for the previous embodiment, but with a different measurable outcome. In this embodiment, an effective amount of the CXCR3 agonist is an increase in peripheral white blood cells. The density (number per unit volume of blood) of white blood cells can be measured by cell counting or by automated methods for determining the number of white blood cells in a sample of whole blood. A blood sample can also be processed to first isolate the white cells prior to counting, or the white cells can be detected using, e.g., labeled antibodies. An effective amount (e.g., therapeutically effective amount) is an amount that produces any increase above a control level either for the total white blood cell population or for any subpopulation thereof. Yet another embodiment is a method of treating cancer. For example, the method includes the same administration of a CXCR3 agonist as discussed above together with the step of subsequently administering either chemotherapy or radiation therapy to the subject. In this embodiment, an effective amount (e.g., therapeutically effective amount) is any amount that treats cancer, meaning that either the safety or effectiveness of the cancer treatment, i.e., the chemotherapy or radiation therapy, is improved compared to the same therapy without CXCR3 agonist administration.

In a further embodiment, preventive administration of a CXCR3 agonist before chemotherapy or radiotherapy is supplemented with an effective amount of the post-chemotherapy or post-radiation therapy administration of an agent that is antagonistic to CXCR3 activity. Such agents include, but are not limited to, an antagonistic antibody to CXCL9, CXCL10, and/or CXCL11, an siRNA or antisense nucleic acid specific for CXCL9, CXCL10, and/or CXCL11 expression, an antagonistic antibody to CXCR3 (the natural receptor for the CXCL9 ligand), an siRNA or antisense nucleic acid specific for CXCR3 expression, and an antagonist of CXCR3 function (e.g., a small molecule antagonist). Any of these antagonists of CXCL9 or combinations thereof can be used according to the invention. For human subjects, administration of a fully human antibody to human CXCL9 may be used.

The time course of administration can vary, but it is generally beneficial to adjust it to coincide with the time course of the increased expression of CXCR3 ligands following chemotherapy or radiotherapy. That is, for example, if the subject's CXCR3 ligand expression is expected to peak at about 7 days following chemotherapy, then a CXCR3 antagonistic agent can be administered so as to be present in a therapeutically effective amount by day 7, and optionally for one or more days before and after day 7. The CXCR3 antagonistic agent can be delivered in a single dose or in multiple doses, e.g., in daily doses. The agent can be administered, e.g., only on day 0 (the day of chemotherapy or radiotherapy, or exposure to a bone marrow damaging agent), or on one or more subsequent days, such as on days 0, 1, 2, 3, 4, 5, 6, 7, 8, 9, 10, and later, or on any combination of those days. The agent can also be administered every other day, or can be administered as a long acting conjugate, such as a PEGylated antibody.

In variations of this embodiment, different endpoints can be used to determine an effective dose. As for earlier embodiments, one possible endpoint is an increase in bone marrow cell density compared to a control group who does not receive the CXCR3 antagonistic agent. Another possible endpoint is an increase in peripheral white blood cells. A third endpoint is efficacy in treating cancer, wherein an improvement in either safety or effectiveness of the accompanying cancer therapy, i.e., chemotherapy or radiation therapy, is observed compared to a control group.

In yet other embodiments, a CXCR3 agonist is administered prior to the treatment with a chemotherapy agent or radiation, but after the therapy is performed, an effective amount of a CXCR3 antagonistic agent is administered to the subject. The same factors apply as for the previous embodiments with respect to the type of subject, the time course of administering the agent, the type of agent, and the type of endpoint for determining an effective amount.

Related to the embodiments described in the previous paragraph are methods of treating a bone marrow disorder characterized by a reduction in bone marrow cells. Such disorders include aplastic anemia, pancytopenia, thrombocytopenia, leucopenia, neutropenia, and myelofibrosis. Each of these diseases exhibits a reduction in one or more types of bone marrow cells. The cause is often exposure to a damaging agent, such as a chemical agent or toxin, radiation, or a virus. The administration of an effective amount of an agent that is antagonistic to CXCR3 relieves the antimyeologenic effect of CXCR3, and leads to an increase in bone marrow cells, which treats the disease. For these methods, an amount of such agent administered that causes any increase in the number or density of bone marrow cells, in bone marrow tissue found anywhere in the body, is an effective amount. In different embodiments, an effective amount can be an amount that increases the number or density of bone marrow cells by at least 5%, at least 10%, at least 15%, at least 20%, at least 25%, at least 30%, at least 40%, at least 50% or more. The schedule of administration can be selected so as to enhance effectiveness, but generally can be a once daily administration, or more or less frequent administration, for a period of 1, 2, 3, 4, 5, 6, 7, 8, 9, 10 or more days, or until an increase in bone marrow cells or a subset of bone marrow cells is observed. Agents that can be administered with these methods include an antibody to CXCL9, CXCL10, and/or CXCL11, a siRNA or antisense nucleic acid specific for CXCL9, CXCL10, and/or CXCL11, an antagonistic antibody to CXCR3, a siRNA or antisense nucleic acid specific for CXCR3, or a small molecule antagonist of CXCR3.

Further embodiments are compositions and kits that can be used in carrying out the methods outlined above. These compositions include one or more agents for administration either prior to or following chemotherapy or radiotherapy, or exposure to a bone marrow damaging agent. The compositions for administration prior to chemotherapy or radiotherapy can contain, for example, a therapeutically effective amount of a CXCR3 agonist, or an expression vector that expresses a CXCR3 agonist, and also a pharmaceutically acceptable carrier. The compositions for administration subsequent to chemotherapy or radiotherapy can contain, for example, a therapeutically effective amount of a CXCL9, CXCL10, and/or CXCL11 antibody, a CXCL9, CXCL10, and/or CXCL11 siRNA or antisense nucleic acid, a CXCR3 antibody, a CXCR3 siRNA or antisense nucleic acid, or an antagonist of CXCR3, and also a pharmaceutically acceptable carrier. In addition, some embodiments include a kit or pharmaceutical pack containing a therapeutically effective amount of one or more agents for administration prior to chemotherapy or radiotherapy and a therapeutically effective amount of one or more agents for administration following chemotherapy or radiotherapy.

In one aspect, the disease to be treated is a cancer. Chemotherapeutic and/or radiation therapy can be combined with the agents described herein for treating a cancer selected from the group consisting of breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer. Exemplary cancers include breast cancer, melanoma, lung cancer, mesothelioma, thyroid cancer, colon cancer or liver cancer.

Co-Therapy with Additional Myelosuppressive Agents

The compositions and methods of the invention can be combined with administration of one or more additional myelosuppressive agents to further prevent damage to bone marrow, or to increase peripheral white blood cells following subsequent chemotherapy or radiotherapy, or to treat cancer or a bone marrow disorder. One such myelosuppressive agent is CCL3, also known as macrophage inflammatory protein-1 a. It is understood that in addition to a natural form of CCL3, variants such as fragments, mutants, or chemically modified versions of CCL3 can be used as well, provided that they have a myelosuppressive effect. Agents such as CCL3 block the entry of hematopoietic stem cells into the S-phase of the cell cycle. See, e.g., Clemons et al., *Blood*, 92:1532 (1998). In some embodiments, an effective dose of CCL3 or another myelosuppressive agent is administered prior to chemotherapy or radiotherapy in addition to the administration of one or more CXCR3 agonists. In other embodiments, an effective dose of CCL3 or another myelosuppressive agent is administered prior to chemotherapy or radiotherapy, and following chemotherapy or radiotherapy one or more CXCR3 antagonists are administered.

In various embodiments, the compositions can be combined with administration of an IL-1Ra polypeptide to a subject prior to receiving chemotherapy. IL-1Ra is a naturally occurring inhibitor of IL-1 activity, and the molecule has been cloned and expressed in *Escherichia coli* as a recombinant protein. While not wishing to be limited by theory, IL-1Ra has the unique capability of competing with IL-1 for occupancy of IL-1 receptors without being internalized or inducing second signals. IL-1Ra was shown herein to act as an endogenous hematopoietic inhibitor, which was upregulated after chemotherapy. The overexpression of endogenous IL-1Ra is responsible for the observed suppression of hematopoiesis after chemotherapy. Thus, IL-1Ra upregulation may be an important protective response that places the bone marrow in a quiescent stage to guard against further insults from chemotherapeutic agents like 5-FU. Therefore, in one embodiment, IL-1Ra is administered before chemotherapy in addition to one or more CXCR3 agonists in order to prepare the bone marrow to tolerate the toxic effects of chemotherapy by slowing down the rate of proliferation of bone marrow hematopoietic cells. It was also surprisingly discovered that IL-1Ra administration is effective for increasing thrombopoiesis (i.e., platelet production) following chemotherapy. See PCT/CN2007/003215 (filed Nov. 14, 2007), which is incorporated by reference herein in its entirety.

Co-Therapy with Hematopoietic Growth Factors

The compositions and methods of the invention can also be administered together with the administration of a hematopoietic growth factor, such as GM-CSF or G-CSF following chemotherapy or radiotherapy. The hematopoietic growth factor can be a naturally occurring molecule or a fragment, mutant, or chemical modification thereof, provided that the growth factor is effective in either stimulating the proliferation of one or more types of bone marrow stem cell or progenitor cell or promoting the differentiation and development of a stem cell or progenitor cell leading to myelogenesis or hematopoiesis. In some embodiments, prior to chemotherapy or radiotherapy and the administration of a hematopoietic growth factor, one or more CXCR3 agonists are administered. In other embodiments, the administration of a hematopoietic growth factor is accompanied by administration of a CXCR3 antagonist following chemotherapy or radiotherapy.

Expression and Purification of CXCR3 Agonists

General. The mammalian CXCR3 agonists, e.g., mouse or human CXCL9, CXCL10, or CXCL11 protein, can be produced through the application of recombinant DNA technology. Recombinant polynucleotide constructs encoding a polypeptide typically include an expression control sequence operably-linked to the coding sequences of polypeptide, including naturally-associated or heterologous promoter regions. As such, vectors containing one or more nucleic acid sequences encoding a polypeptide are described. For recombinant expression of one or more the polypeptides of the invention, the nucleic acid containing all or a portion of the nucleotide sequence encoding the polypeptide is inserted into an appropriate cloning vector, or an expression vector (i.e., a vector that contains the necessary elements for the transcription and translation of the inserted polypeptide coding sequence) by recombinant DNA techniques well-known in the art and as detailed below. Methods for producing diverse populations of vectors have been described by Lerner et al., U.S. Pat. Nos. 6,291,160; 6,680,192.

In general, expression vectors useful in recombinant DNA techniques are often in the form of plasmids. In the present specification, "plasmid" and "vector" can be used interchangeably as the plasmid is the most commonly used form of vector. However, other forms of expression vectors that are not technically plasmids may be used, such as viral vectors (e.g., replication defective retroviruses, adenoviruses and adeno-associated viruses), which serve equivalent functions. Such viral vectors permit infection of a subject and expression in that subject of a compound. In suitable embodiments, the expression control sequences are eukaryotic promoter systems in vectors capable of transforming or transfecting eukaryotic cells. Once the vector has been incorporated into the appropriate host, the host is maintained under conditions suitable for high level expression of the nucleotide sequences encoding the polypeptide, and the collection and purification of the polypeptide. See generally, U.S. Patent Publication No. 20020199213. These expression vectors are typically replicable in the host organisms either as episomes or as an integral part of the host chromosomal DNA. Commonly, expression vectors contain selection markers, e.g., ampicillin-resistance or kanamycin-resistance, to permit detection of those cells transformed with the desired DNA sequences. Vectors can also encode signal peptide, e.g., pectate lyase, useful to direct the secretion of extracellular polypeptides. See U.S. Pat. No. 5,576,195.

The recombinant expression vectors may comprise a nucleic acid encoding a CXCR3 agonist polypeptide in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, *Gene Expression Technology: Methods in Enzymology* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., CXCR3 agonist polypeptides), include, e.g., but are not limited to, 3-phosphoglycerate kinase and other glycolytic enzymes. Inducible yeast promoters include, among others, promoters from alcohol dehydrogenase, isocytochrome C, and enzymes responsible for maltose and galactose utilization. The expression vectors of the invention can be introduced into host cells to thereby produce polypeptides or peptides, including CXCR3 agonist polypeptides.

The recombinant expression vectors can be designed for expression of a polypeptide in prokaryotic or eukaryotic cells. For example, a CXCR3 agonist polypeptide can be expressed in bacterial cells such as *Escherichia coli*, insect cells (using baculovirus expression vectors), fungal cells, e.g., yeast, or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, e.g. using T7 promoter regulatory sequences and T7 polymerase.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene,* 69:301-315), and pET11d (Studier et al., *Gene Expression Technology: Methods in Enzymology,* 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression in *E. coli* is to express the polypeptide in host bacteria with an impaired capacity to proteolytically cleave the recombinant polypeptide. See, e.g., Gottesman, *Gene Expression Technology: Methods in Enzymology,* 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (see, e.g., Wada, et al., 1992. *Nucl. Acids Res.,* 20:2111-2118). Such alteration of nucleic acid sequences of the invention can be carried out by standard DNA synthesis techniques.

In another embodiment, the CXCR3 agonist polypeptide expression vector is a yeast expression vector. Examples of vectors for expression in yeast *Saccharomyces cerevisiae* include pYepSec1 (Baldari, et al., 1987. *EMBO J.,* 6:229-234), pMFa (Kurjan and Herskowitz, *Cell,* 30:933-943, 1982), pJRY88 (Schultz et al., *Gene,* 54:113-123, 1987), pYES2 (Invitrogen Corporation, San Diego, Calif.), and picZ (InVitrogen Corp, San Diego, Calif.). Alternatively, a polypeptide can be expressed in insect cells using baculovirus expression vectors. Baculovirus vectors available for expression of polypeptides, e.g., CXCR3 agonist polypeptide, in cultured insect cells (e.g., SF9 cells) include the pAc series (Smith, et al., *Mol. Cell. Biol.,* 3:2156-2165, 1983) and the pVL series (Lucklow and Summers, 1989. *Virology,* 170:31-39).

In yet another embodiment, a nucleic acid encoding a polypeptide is expressed in mammalian cells using a mammalian expression vector. Examples of mammalian expression vectors include, e.g., but are not limited to, pCDM8 (Seed, *Nature,* 329:840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the polypeptide of the present invention. See, e.g., Chapters 16 and 17 of Sambrook, et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), in particular promoters of T cell receptors (Winoto and Baltimore, EMBO J. 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation, biolistics or viral-based transfection can be used for other cellular hosts. Other methods used to transform mammalian cells include the use of polybrene, protoplast fusion, liposomes, electroporation, and microinjection (see generally, Sambrook et al., *Molecular Cloning*). Suitable methods for transforming or transfecting host cells can be found in Sambrook, et al., *Molecular Cloning: A Laboratory Manual,* 2nd ed., Cold Spring Harbor Laboratory, Cold Spring Harbor Laboratory Press, Cold Spring Harbor, N.Y., (1989), and other laboratory manuals. The vectors containing the DNA segments of interest can be transferred into the host cell by well known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the polypeptide or can be introduced on a separate vector. Cells stably transfected with the introduced nucleic acid can be identified by drug selection (e.g., cells that have incorporated the selectable marker gene will survive, while the other cells die).

A host cell such as a prokaryotic or eukaryotic host cell in culture, can be used to produce (i.e., express) recombinant CXCR3 agonist polypeptides. In one embodiment, the method comprises culturing the host cell (into which a recombinant expression vector encoding the polypeptide has been introduced) in a suitable medium such that the polypeptide is produced. In another embodiment, the method further comprises the step of isolating the polypeptide from the medium or the host cell. Once expressed, the polypeptides are purified from culture media and host cells. The polypeptide can be purified according to standard procedures of the art, including HPLC purification, column chromatography, gel electrophoresis and the like. In one embodiment, the polypeptide is produced in a host organism by the method of Boss et al., U.S. Pat. No. 4,816,397. Purification of recombinant polypeptides is well known in the art and include ammonium sulfate precipitation, affinity chromatography purification technique, column chromatography, ion exchange purification technique, gel electrophoresis and the like (see, generally, Scopes, *Protein Purification* (Springer-Verlag, N.Y., 1982).

Other sequences, such as an affinity purification tag (e.g. His Tag), a peptide linker sequence, and the like, can also be included in the polypeptide of the present invention. In one embodiment, the polypeptide, is fused to a second protein, which can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins can also be engineered to improve characteristics of the polypeptide. For instance, a region of additional amino acids, particularly charged amino acids, can be added to the N-terminus of the polypeptide to improve stability and persistence during purification from the host cell or subsequent handling and storage. Also, peptide moieties can be added to the polypeptide to facilitate purification. Such regions can be removed prior to final preparation of the polypeptide. The addition of peptide moieties to facilitate handling of polypeptides are familiar and routine techniques in the art. The polypeptide of the invention can be fused to marker sequences, such as a peptide which facilitates purification of the fused polypeptide. In suitable embodiments, the marker amino acid sequence is a hexa-histidine peptide, such as the tag provided in a pQE vector (QIAGEN, Inc. Chatsworth, Calif.), among others, many of which are commercially available. As described in Gentz et al., *Proc. Natl. Acad. Sci. USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984.

In a particular embodiment, a mammalian CXCL9, CXCL10, or CXCL11 protein can be expressed from prokaryotic cells using an expression vector. One suitable vector for expression in *E. coli* cells is pET28a. A nucleotide sequence encoding mammalian CXCL9, CXCL10, or CXCL11, can be inserted into the vector between restriction sites. An inducer such as IPTG can be used to induce a high level of expression, leading to the formation of inclusion bodies containing CXCL9, CXCL10, or CXCL11 polypeptide. The inclusion bodies can be denatured using urea and refolded by urea removal, e.g. by dilution into urea-free buffer.

A one-step purification method for CXCL9, CXCL10, or CXCL11 may be used. The method can be applied, for example, to recombinant CXCL9 expressed in *E. coli* and refolded from inclusion bodies. In one aspect, the method involves separation of solubilized, refolded CXCL9 inclusion body proteins using cation exchange chromatography. Solubilized, refolded CXCL9 inclusion body proteins are bound to an S Sepharose column at a pH below the pI of the CXCL9, allowing other proteins to wash through the column, and the ionic strength is increased to elute the purified CXCL9 protein. Optionally, the purity of the eluted, purified CXCL9 can be ascertained by a method selected from SDS-PAGE, Western blot, and capillary electrophoresis. Further details of purification of CXCL9 are found in PCT/CN2007/000971.

Compared with earlier methods for purification of rMuCXCL9 (e.g., Zhang et al. "Large sale production and purification of murine chemokine monokine induced by IFN-gamma (MIG, CXCL9) in insect cells and its angiostatic effects." 2005. *Progress in Biochem and Biophys* 32: 975-981), these have the advantages of cost effectiveness, a high purity of >99%, requiring only one chromatography step, and no use of toxic components such as dithiothreitol (DTT). Although DTT stabilizes proteins that possess free sulfhydryl groups during the refolding of recombinant proteins, it may interfere with the redox system. Addition of DTT in the refolding buffer of rMUCXCL9 led to protein aggregation. On the other hand, the purified rMuCXCL9 in the storage buffer without DTT was stable, and its chemoattractant activity was retained for over 3 months at 4° C., even in the presence of high salt.

In some embodiments, the amino acid Asp can be added before the mature rMuCXCL9 protein to fit the NcoI site in the vector. Asp is a strongly acidic amino acid and reduces the pI of the protein to 10.52 from 10.62. According to the N-end rule, the in vivo half-life of a protein is related to its N-terminal residue. Thus, a CXCL9 protein with an N-terminal Asp has a half-life of greater than 10 h in *E coli* at 36° C., but only 3 min in *S. cerevisiae* at 30° C. (see Tobias et al. 1991 *Science* 254:1374-1377; Varshaysky 1997. *Genes Cells* 2:13-28).

Antibodies

The CXCR3 antagonists may include antibodies capable of binding to CXCR3 or a natural ligand of CXCR3 (e.g., CXCL9, CXCL10, and CXCL11), thereby interfering with the activity of CXCR3 or interfering with the binding of the ligand with the receptor. An antibody is an immunoglobulin molecule immunologically reactive with a particular antigen, and includes both polyclonal and monoclonal antibodies. An antibody includes genetically engineered forms such as chimeric antibodies (e.g., humanized murine antibodies) and heteroconjugate antibodies (e.g., bispecific antibodies). Antibodies also include antigen-binding forms of antibodies, including fragments with antigen-binding capability (e.g., Fab', F(ab')$_2$, Fab, Fv and rIgG. See also, *Pierce Catalog and Handbook*, 1994-1995 (Pierce Chemical Co., Rockford, Ill.). See also, e.g., Kuby, J., *Immunology*, 3rd ed., W. H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al., *J. Immunol.*, 148:1547 (1992), Pack and Pluckthun, *Biochemistry*, 3(1):1579 (1992), Zhu et al., *Protein Sci.*, 6:781 (1997), Hu et al., *Cancer Res.*, 56:3055 (1996), Adams et al., *Cancer Res.*, 53:4026 (1993), and McCartney et al., *Protein Eng.*, 8:301 (1995).

An antibody immunologically reactive with a particular antigen can be generated by recombinant methods such as selection of libraries of recombinant antibodies in phage or similar vectors, see, e.g., Huse et al., *Science*, 246:1275-1281 (1989); Ward et al., *Nature*, 341:544-546 (1989); and Vaughan et al., *Nature Biotech.*, 14:309-314 (1996), or by immunizing an animal with the antigen or with DNA encoding the antigen.

Typically, an immunoglobin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs." The extent the framework regions and CDRs have been defined. The sequences of the framework regions of different light or heavy chains are relatively conserved within a species. The framework regions of an antibody, that is the combined framework regions of the constituent light and heavy chains, serves to position and align, the CDRs in three dimensional space.

The CDRs primarily responsible for binding to an epitope of an antigen. The CDRs of each chain are typically referred to as CDR1, CDR2 and CDR3 numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "$V_H$" refer to the variable region of an immunoglobulin heavy chain of an antibody, including the heavy chain of an Fv, scFv, dyFv (disulfide-stabilized Fv) or Fab. References to "$V_L$" or a "$V_L$" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active antigen binding site.

In one aspect, an antibody can be a "chimeric antibody". For example, a chimeric antibody is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one aspect, an antibody can be a "humanized antibody". For example, a humanized antibody is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a immunoglobulin consensus sequence. The humanized antibody optimally also will comprise at least a portion of an immunoglobulin constant region (Fc), typically that of a human immunoglobulin (Jones et al., *Nature*, 321:522-525 (1986); Riechmann et al., *Nature*, 332:323-329 (1988); and Presta, *Curr. Op. Struct. Biol.*, 2:593-596 (1992)). Humanization can be essentially performed following the method of Winter and co-workers (Jones et al., *Nature*, 321: 522-525 (1986); Riechmann et al., *Nature*, 332:323-327 (1988); Verhoeyen et al., *Science*, 239:1534 1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

In one aspect, an antibody can be a "human antibody" or "fully human antibody," which can refer to an immunoglobulin comprising human variable regions in addition to human framework and constant regions. Such antibodies can be produced using various techniques known in the art. For example in vitro methods involve use of recombinant libraries of human antibody fragments displayed on bacteriophage (e.g., McCafferty et al., *Nature*, 348:552-554 (1990); Hoogenboom & Winter, *J. Mol. Biol.*, 227:381 (1991); and Marks et al., *J. Mol. Biol.*, 222:581 (1991)), yeast cells (Boder and Wittrup, *Nat. Biotechnol.*, 15:553-557 (1997), or ribosomes (Hanes and Pluckthun, *Proc. Natl. Acad. Sci. USA*, 94:4937-4942 (1997)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584, 5,545,807; 5,545,806; 5,569,825; 5,625,126; 5,633,425; 5,661,016, and in the following scientific publications: (e.g., Jakobavits, *Adv. Drug. Dcliv. Rev.*, 31:33-42 (1998), Marks et al., *Bio/Technology*, 10:779-783 (1992); Lonberg et al., *Nature*, 368:856-859 (1994); Morrison, *Nature*, 368:812-13 (1994); Fishwild et al., *Nature Biotechnology*, 14:845-51 (1996); Neuberger, *Nature Biotechnology*, 14:826 (1996); Lonberg & Huszar, *Intern. Rev. Immunol.*, 13:65-2593 (1995).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, at least 6, or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed (1996).

Antigen or "Ag" refers to a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen." Furthermore, one skilled in the art will understand that an antigen need not be encoded solely by a full length nucleotide sequence of a gene. It is readily apparent that the use of partial nucleotide sequences of more than one gene and that these nucleotide sequences are arranged in various combinations to elicit the desired immune response. Moreover, a skilled artisan will understand that an antigen need not be encoded by a "gene" at all. An antigen can be synthesized or can be derived from a biological sample.

An antibody can be bound (or linked, or conjugated), either covalently, through a linker or a chemical bond, or noncovalently, through ionic, van der Waals, electrostatic, or hydrogen bonds, to an effector molecule. The effector molecule can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard" e.g., beta radiation.

For example, an antibody can be conjugated to a "label" or a "detectable moiety." Generally, a label or detectable moiety can be a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, $^3$H, $^{14}$C, $^{32}$P, $^{35}$S, or $^{125}$I. In some cases, the radioisotopes are used as toxic moieties, as described below. The labels may be incorporated into the nucleic acids, proteins and antibodies at any position. Any method known in the art for conjugating the antibody to the label may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982). The lifetime of radiolabeled peptides or radiolabeled antibody compositions may extended by the addition of substances that stabilize the radiolabeled peptide or antibody and protect it from degradation. Any substance or combination of substances that stabilize the radiolabeled peptide or antibody may be used including those substances disclosed in U.S. Pat. No. 5,961,955.

The phrase "specifically (or selectively) binds" to an antibody or antigen, such as a protein, suitably a CXCR3, CXCL9, CXC10, or CXCL11 protein or "specifically (or selectively) immunoreactive with," when referring to a protein or peptide or antibody, can refer to a binding reaction that is determinative of the presence of the protein in a heterogeneous population of proteins and other biologics. Thus, under designated immunoassay conditions, the specified antibodies bind to a particular protein at least two times the background and more typically more than 10 to 100 times background.

Antibodies that are immunoreactive with CXCR3, CXCL9, CXC10, or CXCL11 proteins and not with other proteins can be prepared, for example, by subtracting out antibodies that cross-react with other molecules. A variety of immunoassay formats may be used to select antibodies specifically immunoreactive with a particular protein. For example, solid phase ELISA immunoassays are routinely used to select antibodies immunoreactive only with a particular protein (see, e.g., Harlow & Lane, *Antibodies, A Laboratory Manual* (1988), for a description of immunoassay formats and conditions that can be used to determine specific immunoreactivity).

Dosage and frequency of the administration of antibodies vary depending on the half-life of the antibody in the patient. The half-life of a CXCR3, CXCL9, CXC10, or CXCL11 antibody can also be prolonged via fusion to a stable polypeptide or moiety, e.g., albumin or PEG. The methods and techniques for producing fusion antibodies are well known in the art and can be used in conjunction with an antibody of the invention. Examples of method and techniques for producing a fusion protein or antibody are generally described by U.S. Pat. Nos. 7,081,354, 6,972,322, 7,041,478 and 6,987,006.

In general, humanized antibodies show the longest half-life, followed by chimeric antibodies and nonhuman antibodies. In one aspect, the antibody, or antigen-binding fragments, variants, or derivatives thereof of the invention can be administered in unconjugated form. In another aspect, the antibody, or antigen-binding fragments, variants, or derivatives thereof can be administered multiple times in conjugated form. In still another aspect, the antibodies, or antigen-binding fragments, variants, or derivatives thereof can be administered in unconjugated form, then in conjugated form, or vice versa.

An antibody can be, in addition to a natural immunoglobulin, any antigen-binding fragment of an immunoglobulin or a modified immunoglobulin or antigen-binding fragment. Antibodies can be modified, for example, by the covalent attachment of an organic moiety. Such modification can produce an antibody with improved pharmacokinetic properties (e.g., increased in vivo plasma half-life). The organic moiety can be a linear or branched hydrophilic polymeric group, fatty acid group, or fatty acid ester group. In particular embodiments, the hydrophilic polymeric group can have a molecular weight of about 800 to about 120,000 daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

An antibody can comprise one or more organic moieties that are covalently bonded, directly or indirectly, to the antibody. Each organic moiety that is bonded to an antibody or antigen-binding fragment can independently be a hydrophilic polymeric group, a fatty acid group or a fatty acid ester group. A fatty acid can be a mono-carboxylic acid or a di-carboxylic acid. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies can be linear or branched and include, for example, polyalkane glycols (e.g., PEG, monomethoxypolyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody has a molecular weight of about 800 to about 150,000 Daltons as a separate molecular entity. For example, $PEG_{5000}$ and $PEG_{20,000}$ wherein the subscript is the average molecular weight of the polymer in daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for antibodies can be saturated or can contain one or more units of unsaturation. Fatty acids that are suitable for modifying antibodies of the invention include, for example, n-dodecanoate (C12, laurate), n-tetradecanoate (C14, myristate), noctadecanoate (C18, stearate), n-eicosanoate (C20, arachidate), n-docosanoate (C22, behenate), n-triacontanoate (C30), n-tetracontanoate (C40), cis-Δ-octadecanoate (C18, oleate), all cisΔ5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The antibodies can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press, San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated malamide derivative of the fatty acid. (see, for example, Thompson, et al., WO 92/16221.)

Conjugated antibodies can be produced by reacting an antibody or antigen binding fragment with a modifying agent. For example, the organic moieties can be bonded to the antibody in a non-site specific manner by employing an amine-reactive modifying agent, for example, an NHS ester of PEG. Conjugated antibodies or antigen-binding fragments can also be prepared by reducing disulfide bonds (e.g., intra-chain disulfide bonds) of an antibody or antigen binding fragment. The reduced antibody or antigen-binding fragment can then be reacted with a thiol-reactive modifying agent to produce the modified antibody of the invention. Conjugated antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996). Other methods and techniques for conjugating antibodies that can be performed with the antibodies of the invention are generally described by U.S. Pat. Nos. 6,426,086, 6,071,533, 6,214,388, 4,429,008 and European Patent No. EP 172435.

Binding affinity for a target antigen is typically measured or determined by standard antibody-antigen assays, such as Biacore competitive assays, saturation assays, or immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 µM, preferably <100 nM, and most preferably <0.1 nM. Antibody molecules will typically have a KD in the lower ranges. $K_D$=[Ab-Ag]/[Ab] [Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds.

In some embodiments, the antibodies may specifically bind to CXCR3, CXCL9, CXCL10, or CXCL11 proteins. By "specifically bind" herein is meant that the antibodies bind to the CXCR3, CXCL9, CXCL10, or CXCL11 protein with a $K_D$ of at least about 0.1 mM, more usually at least about 1 µM, preferably at least about 0.1 .µM or better, and most preferably, 001 µM or better.

Small Interfering RNA (siRNA)

A small interfering RNA (siRNA) is an RNA molecule comprising a set of nucleotides that is targeted to a gene or polynucleotide of interest. As used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein.

An siRNA in the form of a double stranded polynucleotide comprises about 18 base pairs, about 19 base pairs, about 20 base pairs, about 21 base pairs, about 22 base pairs, about 23 base pairs, about 24 base pairs, about 25 base pairs, about 26 base pairs, about 27 base pairs, about 28 base pairs, about 29 base pairs or about 30 base pairs in length. In suitable embodiments, the double stranded siRNA may be capable of interfering with the expression and/or the activity of a CXCL9, CXCL10, CXCL11, and/or CXCR3.

A single stranded siRNA comprises a portion of an RNA polynucleotide sequence that is targeted to a gene or polynucleotide of interest. A single stranded siRNA comprises a polynucleotide of about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides or about 30 nucleotides in length. The single stranded siRNA is capable of interfering with expression and/or activity of a target polynucleotide or a variant thereof. In suitable embodiments, the single strand siRNA is also capable of annealing to a complementary sequence to result in a dsRNA that is capable of interfering with the expression and/or the activity of a CXCL9, CXCL10, CXCL11, and/or CXCR3.

In yet another aspect, the siRNA comprises a polynucleotide comprising either a double stranded or a single stranded polynucleotide, wherein the siRNA has one, two, three, four or more nucleotide alterations or substitutions therein.

A siRNA polynucleotide is an RNA nucleic acid molecule that interferes with RNA activity that is generally considered to occur via a post-transcriptional gene silencing mechanism. A siRNA polynucleotide typically comprises a double-stranded RNA (dsRNA) but is not intended to be so limited and may comprise a single-stranded RNA (see, e.g., Martinez et al., *Cell*, 110:563-74 (2002)). The siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that exemplary sequences disclosed as DNA sequences capable of directing the transcription of the siRNA polynucleotides are also intended to describe the corresponding RNA sequences and their complements, given the well established principles of complementary nucleotide base-pairing.

A siRNA may be transcribed using as a template a DNA (genomic, cDNA, or synthetic) that contains a promoter for an RNA polymerase promoter. For example, the promoter can be the U6 promoter or the H1 RNA polymerase III promoter. Alternatively, the siRNA may be a synthetically derived RNA molecule. In certain aspects, the siRNA polynucleotide may have blunt ends. In certain other aspects, at least one strand of the siRNA polynucleotide has at least one or two nucleotides that "overhang" (i.e., that do not base pair with a complementary base in the opposing strand) at the 3' end of either strand of the siRNA polynucleotide. In a preferred aspect of the invention, each strand of the siRNA polynucleotide duplex has a two-nucleotide overhang at the 3' end. The two nucleotide overhang may be a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., International Publication No. WO 01/75164.

Suitable siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other aspects about 19, about 20, about 21, about 22 or about 23 base pairs, or about 27 base pairs, whereby the use of "about" indicates that in certain aspects and under certain conditions the processive cleavage steps that may give rise to functional siRNA polynucleotides that are capable of interfering with expression of a selected polypeptide may not be absolutely efficient. Hence, siRNA polynucleotides, may include one or more siRNA polynucleotide molecules that may differ (e.g., by nucleotide insertion or deletion) in length by one, two, three, four or more base pairs as a consequence of the variability in processing, in biosynthesis, or in artificial synthesis of the siRNA. The siRNA polynucleotide may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In one aspect, the siRNA polynucleotides are homogeneous with respect to a specific nucleotide sequence.

Polynucleotide variants may contain one or more substitutions, additions, deletions, and/or insertions such that the activity of the siRNA polynucleotide is not substantially diminished. The effect of any such alterations in nucleotide content on the activity of the siRNA polynucleotide may generally be assessed as described elsewhere herein. Variants preferably exhibit at least about 75%, 78%, 80%, 85%, 87%, 88% or 89% identity and more preferably at least about 90%, 92%, 95%, 96%, or 97% identity to a portion of a polynucleotide sequence that encodes a native CXCR3, CXCL9, CXCL10, or CXCL11. The percent identity may be readily determined by comparing sequences of the polynucleotides to the corresponding portion of the target polynucleotide, using any method including using computer algorithms well known to those having ordinary skill in the art. These include the Align or the BLAST algorithm (Altschul, *J. Mol. Biol.,* 219:555-565 (1991); Henikoff and Henikoff, *Proc. Natl. Acad. Sci. USA,* 89:10915-10919 (1992)).

Certain siRNA polynucleotide variants can be substantially homologous to a portion of a polynucleotide encoding a target polypeptide. Single-stranded polynucleotides derived from these polynucleotide variants are capable of hybridizing under moderately stringent conditions to a naturally occurring DNA or RNA sequence encoding the target polypeptide. An siRNA polynucleotide that detectably hybridizes to the polynucleotide sequence encoding the target polypeptide under moderately stringent conditions may have a nucleotide sequence that includes at least 10 consecutive nucleotides, or 11, 12, 13, 14, 15, 16, 17, 18, 19, 20, 21, 22, 23, 24, 25, 26, 27, 28, 29 or 30 consecutive nucleotides that are complementary to a particular target polynucleotide. In certain aspects, such a siRNA sequence (or its complement) will be unique to a single particular polynucleotide encoding the target polypeptide for which interference with expression is desired. In certain other aspects, the sequence (or its complement) may be shared by two or more related polynucleotides encoding the target polypeptide for which interference with polypeptide expression is desired.

Suitable moderate stringent conditions include, for example, pre-washing the polynucleotide in a solution of 5×SSC, 0.5% SDS, 1.0 mM EDTA (pH 8.0); hybridizing the polynucleotide at 50° C.-70° C., 5×SSC for 1-16 hours (e.g., overnight); followed by washing the polynucleotide once or twice at 22-65° C. for 20-40 minutes with one or more each of 2×, 0.5× and 0.2×SSC containing 0.05-0.1% SDS. For additional stringency, hybridization conditions may include an additional wash in 0.1×SSC and 0.1% SDS at 50-60° C. for 15-40 minutes. Those of ordinary skill in the art will understand that, variations in stringency of hybridization conditions may be achieved by altering the time, temperature, and/or concentration of the solutions used for the pre-hybridization, hybridization, and wash steps. Suitable conditions may also depend in part on the particular nucleotide sequences of the probe used, and of the blotted, proband nucleic acid sample. Accordingly, it will be appreciated that suitably stringent conditions can be readily selected, without undue experimentation, when a desired selectivity of the polynucleotide is identified, based on its ability to hybridize to one or more certain proband sequences while not hybridizing to certain other proband sequences.

Sequence specific siRNA polynucleotides may be designed using one or more of several criteria. For example, to design an siRNA polynucleotide that has about 21 consecutive nucleotides identical to a sequence encoding a polypeptide of interest, the open reading frame of the polynucleotide sequence may be scanned for about 21-base sequences length that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 16 consecutive nucleotides not identified as being present in any other known polynucleotide sequence. Alternatively, an siRNA polynucleotide sequence may be designed and chosen using a computer software available commercially from various vendors, e.g., OligoEngine™ (Seattle, Wash.); Dharmacon, Inc. (Lafayette, Colo.); Ambion Inc. (Austin, Tex.); and QIAGEN, Inc. (Valencia, Calif.)). See also Elbashir et al., *Genes & Development*, 15:188-200 (2000); Elbashir et al., *Nature*, 411:494-98 (2001). The siRNA polynucleotide may then be tested for the ability to interfere with the expression of the target polypeptide according to methods known in the art and described elsewhere in herein. The determination of the effectiveness of an siRNA polynucleotide includes not only consideration of its ability to interfere with the expression of the target polypeptide, but also whether the siRNA polynucleotide is toxic to the host cell. For example, a desirable siRNA would exhibit an RNA interference activity and would also not exhibit an unwanted biological consequence. An example of an unwanted biological consequence is apoptosis of a cell for which cell death is not a desired as a result of the introduction of the siRNA into the host cell.

Based on the present disclosure, it should be appreciated that the siRNAs may effect silencing of the target polypeptide expression to different degrees. The siRNAs thus must first be tested for their effectiveness. Selection of siRNAs are made therefrom based on the ability of a given siRNA to interfere with or modulate the expression of the target polypeptide. Accordingly, identification of specific siRNA polynucleotide sequences that are capable of interfering with expression of a desired target polypeptide requires production and testing of each siRNA. Since not all siRNAs that interfere with protein expression will have a physiologically important effect, the present disclosure also sets forth various physiologically relevant assays for determining whether the levels of interference with target protein expression using the siRNAs of the invention have clinically relevant significance.

siRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated with other molecules to improve their stability and/or delivery properties.

Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful). In addition, an siRNA polynucleotide may be administered to a mammal, as may be a DNA sequence (e.g., a recombinant nucleic acid construct as provided herein) that supports transcription (and optionally appropriate processing steps) such that a desired siRNA is generated in vivo.

In one aspect, an siRNA polynucleotide is provided, wherein the siRNA polynucleotide is capable of interfering with expression of a target polypeptide can be used to generate a silenced cell. Any siRNA polynucleotide that, when contacted with a biological source for a period of time, results in a significant decrease in the expression of the target polypeptide is included in the invention. In some embodiments, the decrease is greater than about 10%, greater than about 20%, greater than about 30%, greater than about 40%, about 50%, about 60%, about 70%, about 75%, about 80%, about 85%, about 90%, about 95% or about 98% relative to the expression level of the target polypeptide detected in the absence of the siRNA. In some embodiments, the presence of the siRNA polynucleotide in a cell does not result in or cause any undesired toxic effects, for example, apoptosis or death of a cell in which apoptosis is not a desired effect of RNA interference.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., *Tetrahedron Lett.*, 28:3539-3542 (1987); Stec et al., *Tetrahedron Lett.*, 26:2191-2194 (1985); Moody et al., *Nucleic Acids Res.*, 12:4769-4782 (1989); Eckstein, *Trends Biol. Sci.*, 14:97-100 (1989); Stein, *In: Oligodeoxynucleotides. Antisense Inhibitors of Gene Expression*, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' o-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

Antisense Nucleic Acids

In one aspect, the invention provides for use of antisense nucleic acids as CXCR3 antagonists. Antisense generally refers particularly to the nucleic acid sequence of the non-coding strand of a double stranded DNA molecule encoding a polypeptide, or to a sequence which is substantially homologous to the non-coding strand. An antisense sequence is complementary to at least a portion of the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

Gene Therapy

For a review of gene therapy procedures, see Anderson, *Science*, 256:800-013 (1992); Nabel and Feigner *TIBTECH*, 11:211-217 (1993); Mitani and Caskey, *TIBTECH*, 11:162-166 (1993); Mulligan, *Science*, 926-932 (1993); Dillon, *TIBTECH*, 11:167-175 (1993); Miller, *Nature*, 357:455-460 (1992); Van Brunt, *Biotechnology*, 6(10):1149-1154 (1988); Viguo, *Restorative Neurology and Neuroscience*, 8:35-36 (1995); Kremer and Perricaudet, *British Medical Bulletin*, 51(1):31-44 (1995); Haddada et al., *Current Topics In Microbiology And Immunology*, Doerflorand Boehm (eds.) Springer-Verlag, Heidelberg Germany (1995); and Yu et al., *Gene Therapy*, 1:13-26 (1994).

Delivery of the gene or genetic material into the cell is the first step in gene therapy treatment of disease. A large number of delivery methods are well known to those of skill in the art. Such methods include, for example lipomome-based gene delivery (Debs and Zhu, WO 93/24640 (1993); Mannino and Gould-Fogerite, *BioTechniques*, 6(7):682-691 (1993); Rose, U.S. Pat. No. 5,279,833; Brigham, WO 91/06309 (1991); and Feigner et al., *Natl. Acad. Sci. USA*, 84:7413-7414 (1991), and replication-defective retroviral vectors harboring a therapeutic polynucleotide as part of the retroviral genome (see, e.g., Miller et al., *Mol. Cell. Biol.*, 10:4239 (1990); Kolberg, *J. NIH Res.*, 4:43 (1992), and Cornetta et al., *Hum. Gene*

*Ther.,* 2:215 (1991)). Widely used retroviral vectors include those based upon murine leukemia virus (MuLV), gibbon ape leukemia virus (OuLV), Simian Immunodeficiency virus (SIV), human immuno deficiency virus (HIV), and combinations thereof. See, e.g., Buchscher et al., *J. Virol.,* 66(5) 2731-2739 (1992); Johannu et al., *J. Virol.,* 66(5):1635-1640 (1992); Sommerfelt et al., *J. Virol.,* 176:58-59 (1990); Wilson et al., *J. Virol.,* 63:2374-2370 (1990); Miller et al., *J. Virol.,* 65:2220-2224 (1991); WongStaal et al., PCT/US94/05700, and Rosenburg and Fauci, *Fundamental Immunology,* Third Edition Paul (ed.) Raven Press, Ltd., New York (1993) and the references therein.)

AAV-based vectors are also used to transduce cells with target nucleic acids, e.g., in the in vitro production of nucleic acids and peptides, and in in vivo and ex vivo gene therapy procedures. See, West et al., *Virology,* 160:38-47 (1987); Carter et al., U.S. Pat. No. 4,797,368 (1989); Carter et al., WO93/24641 (1993); Kotin, *Human Gene Therapy,* 5:793-801 (1994); Muzyczka, *J. Clin. Invest.,* 94:1351 (1994); and Samulski, supra, for an overview of AAV vectors. Construction of recombinant AAB vectors are described in a number of publications, including Lebkowski, U.S. Pat. No. 5,173,414; Tratschin et al., *Mot. Cell. Biol.,* 5(11):3251-3260 (1985); Tratschin, et al., *Mot. Cell. Biol.,* 4:2072-2081 (1985); Hermonat and Muzyczka, *Proc. NatiAcad. Sci. USA,* 81:6466-6470 (1984); McLaughlin et al. (1988), and Samulski et al., *J. Virol.,* 63:03822-3828 (1989).

Gene therapy methodologies can be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, and the transfected cells are expanded in number and then reimplanted in the patient. For in vitro gene transfer, the method is the same, but the transfected cells are cells growing in culture, such as tissue culture cells, and not cells from the individual patient. In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed.

Additionally, the other methods described herein, such as use mechanical or chemical methods may be used for in vivo insertion of the nucleic acids of the invention.

Mechanical methods of DNA delivery include direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue. Chemical methods of gene therapy may involve a chemical to bind to the cell and/or ferry the DNA across the cell membrane, such as fusogenic lipid vesicles such as liposomes or other vesicles for membrane fusion, lipid particles of DNA incorporating cationic lipid such as lipofectin, or polylysine mediated transfer of DNA. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells and can be engineered to comprise the alternative splicing vector of; the present invention. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols (see e.g., Eck, S. L. and J. M. Wilson, "Gene Based Therapy," Goodman & Gilmer's *The Pharmacological Basis of Therapeutics,* 8th ed.:77-101, McGraw-Hill, New York (1996)). To direct tissue specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site-specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include, but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors and adenoviral vectors are the most widely utilized gene transfer vectors. Murine leukemia retroviruses are composed of a single strand RNA complexed with a nuclear core protein and polymerase (pot) enzymes, encased by a protein core (gag) and surrounded by a glycoprotein envelope (env) that determines host range. The genomic structure of retroviruses include the gag, pot, and env genes enclosed at by the 5' and 3' long terminal repeats (LT11).

Retroviral vector systems exploit the fact that a minimal vector containing the 5' and 3' LTRs and the packaging signal are sufficient to allow vector packaging, infection and integration into target cells providing that the viral structural proteins are supplied in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long-term expression of heterologous genes in vivo in some cell types.

Adenoviral vectors are derived from replication incompetent adenoviruses, which are typically contain a deletion in the El gene. Such vectors are transfected into cells, such as the 293 human embryonic kidney 1 cell line, which allow replication of El deleted adenoviruses. After transfection, the adenoviral vector is allowed to replicate in these specialized helper cells and form infectious particles, which are collected and purified.

Plasmids for transfection of mammalian cells for in vivo gene therapy include, for example, pRSVCAT, construction of this plasmid is described in Gorman et al., *Proc. Nat. Acad. Sciences USA,* 79:6777-6781 (1982); p5'L3-CAT, construction of this plasmid is described in Sakai et al., *Genes and Development,* 2:1144-1154 (1982); pSIS-CAT: construction of this plasmid is described in Huang and Gorman, *Nucleic Acids Research,* 18:937-948 (1990); pSVL; pMSG (Pharnzucio, Uppsala, Sweden); pSV2dhfr (ATCC 37146); pBC12MI (ATCC 67109) pCMVSport 210; and pCMVSprot 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

In one aspect, a therapeutic of the present invention can be used to treat bone marrow cells ex vivo. Such treatment is routinely contemplated in the treatment of a variety of disease states, including in individuals who require bone marrow transplants (e.g., patients with aplastic anemia, acute leukemias, recurrent lymphomas, or solid tumors).

Ex vivo cell transfection for diagnostics, research, or for gene therapy (e.g., via re-infusion of the transfected cells into the host organism) is well known to those of skill in the art. For example, the cells are isolated from the subject organism, transfected with a gene or cDNA, and re-infused back into the subject organism (e.g., patient). Various cell types suitable for ex vivo transfection are well known to those of skill in the art (see, e.g., Freshney et al., *Culture of Animal Cells, a Manual of Basic Technique,* third ed., Wiley-Liss, New York (1994)), and the references cited therein for a discussion of how to isolate and culture cells from patients). In humans, bone marrow aspirations from iliac crests are performed e.g., under general anesthesia in the operating room. Following transfection of the bone marrow cells ex vivo, they are injected intravenously back into the patient.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

These methods described herein are by no means all-inclusive, and further methods to suit the specific application will be apparent to the ordinary skilled artisan. Moreover, the effective amount of the compositions can be further approximated through analogy to compounds known to exert the desired effect.

Chemotherapeutic Agents

In some embodiments, the methods include the administration of a chemotherapeutic agent after the administration of a CXCR3 agonist and/or before administration of a CXCR3 antagonist. Chemotherapeutic agents include alkylating agents, antimetabolites, natural products such as plant alkaloids and biologics. Alkylating agents bind covalently to DNA to inhibit DNA synthesis and stop cell growth. Suitable alkylating agents include, but are not limited to, nitrogen mustards such as chlorambucil, cyclophosphamide, estramustine, ifosfamide, mechlorethamine and melphalan, aziridine derivatives such as thiotepa, alkyl sulfonates such as busulfan and nitrosoureas, such as carmustine.

Antimetabolites are agents that block the biosynthesis or use of normal cellular metabolites. Similar to alkylating agents, antimetabolites inhibit DNA synthesis. However, antimetabolites are more effective against slower growing tumors than alkylating agents. Suitable antimetabolites include, but are not limited to, folate analogs such as methotrexate, purine analogs such as fludarabine, mercaptopurine and thioguanine, adenosine analogs such as cladribine and pentostatin and pyrimidine analogs such as capecitabine, cytarabine, depo-cyt, floxuridine and fluorouracil.

A third class of chemotherapeutic agents are natural products such as antitumor antibiotics. Suitable antitumor antibiotics include, but are not limited to, bleomycin, dactinomycin, daunorubicin, doxorubicin, doxil, epirubicin, idarubicin, mitomycin and mitoxantrone.

Other natural products include the vinca alkaloids which arrest cell division by preventing the formation of the mitotic spindle through disaggregation of microtubules. Suitable vinca alkaloids include, but are not limited to, vincristine, vinblastine, vinorelbine and vindesine. Taxanes are another type of natural product chemotherapeutic agent. Taxanes include, but are not limited to paclitaxel and docetaxel. The taxanes stabilize microtubules to inhibit mitotic spindle assembly to prevent cell division.

Biologics are yet another class of chemotherapeutic agents, and encompass monoclonal antibodies, soluble receptors, protein-chemotherapeutic conjugates, antisense oligonucleotides, and the like. Example of such agents include, Avastin® (bevacizumab), Campath® (alemtuzumab), Erbitux® (cetuximab), Herceptin® (trasturtnnab), Rituxan (rituximab), Zevalin™ (ibritumomab tiuxetan), BEXXAR® (Tositumomab and 1-131 tositumomab; monoclonal antibody targeting the CD20 antigen and radiolabeled version of the antibody), Mylotarg™(gemtuzumab ozogamicin).

The chemotherapeutic agents described above can be either cell cycle dependent or cell cycle independent. An agent is cell cycle dependent it its effectiveness depends on which stage of the cell cycle the target (cancer) and non target (normal) cells are in when the agent is administered. For example, alkylating agents are generally cell cycle dependent, because they are selectively toxic for cells during the S-phase. Cell cycle independent chemotherapeutic agents have approximately equal toxicity at all stages of the cell cycle. An antibody to a tumor antigen, especially if labeled with a toxin or a radioisotope, is likely to be cell cycle independent.

Radiation Therapy

In some embodiments, the methods include the administration of a radiation therapy after the administration of a CXCR3 agonist and/or before administration of a CXCR3 antagonist. Radiation therapy (radiotherapy) can be used to treat almost every type of solid tumor, including brain, breast, cervix, larynx, lung, pancreas, prostate, skin, spine, stomach, uterus cancers, or soft tissue sarcomas. The appropriate dosage of radiation depends on a number of factors, including the type of cancer, type of radiation treatment, as well as proximity of radiation therapy to tissues and organs nearby that may be damaged by radiation, and tolerances of those tissues and organs to radiation. For example, radiation doses range from a low of 65 Gy to a high of 81 Gy for the treatment of prostate cancer, while for the treatment of solid epithelial tumors, the dosage can range between 50 Gy and 70 Gy. In contrast, lymphomas typically receive lower doses, ranging between 20 to 40 Gy in daily doses.

Radiation therapies which are suitable for use in the combination treatments described herein, include the use of (a) external beam radiation; and (b) a radiopharmaceutical agent which comprises a radiation-emitting radioisotope.

External beam radiation therapy for the treatment of cancer uses a radiation source that is external to the patient, typically either a radioisotope, such as $^{60}$Co, $^{137}$Cs or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabeled pharmaceutical agent, for example, a radiolabeled antibody, contains a radioisotope (RI) which serves as the radiation source. As contemplated herein, the term "radioisotope" includes metallic and nonmetallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth-212, Bismuth213, Cadmium-109, Cadmium-15m, Calcium-45, Cerium-139, Cerium-141, Cerium-144, Cesium-137, Chromium-51, Cobalt-55, Cobalt-56, Cobalt-57, Cobalt 58, Cobalt-60, Cobalt 64, Copper-60, Copper-62, Copper-64, Copper-67, Erbium-169, Europium-152, Gallium-64, Gallium-67, Gallium-68, Gadolinium-153, Gadolinium-157 Gold-195, Gold-199, Hafnium-175, Hafnium-175-181, Holmium-166, Indium-110, Indium-1 11, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium/17, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (nonmetallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

In suitable embodiments, the physical half-life of the therapeutic radioisotope should be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life would cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

The type of radiation that is suitable for use in the methods can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., *Textbook of Radiation Oncology* (1998) (pubs. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., *Combined Treatment with Radiooestradiol lucanthone in Mouse C3HBA Mammary Adenocarcinoma and with Estradiol lucanthone in an Estrogen, Bioassay, Int. J. Radiat. Oncol. Biol. Phys.* 7:347-357 (1981). Other radiation delivery methods can be used in the practice of this invention.

Dosage and Formulation of Pharmaceutical Compositions

The present invention envisions treating a disease or condition, for example, cancer, in a subject by the administration of CXCR3 agonist or antagonist compositions in conjunction with chemotherapy or radiation therapy. Administration of the CXCR3 agonist or antagonist compositions in accordance with the present invention may be continuous or intermittent, depending, for example, upon the recipient's physiological condition, whether the purpose of the administration is therapeutic or prophylactic, and other factors known to skilled practitioners. The administration of the vaccines of the invention may be essentially continuous over a preselected period of time or may be in a series of spaced doses.

In one embodiment, the CXCR3 agnosits or antagonists are administered directly to a subject to achieve the desired response. The amount administered will vary depending on factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art.

Typically, an effective amount of the compositions of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For administration of CXCR3 agonist or antagonist, the dosage ranges from about 0.0001 to 100 mg/kg, and more usually 0.01 to 5 mg/kg every day, every two days or every three days. For example dosages can be 0.1 mg/kg body weight or 1 mg/kg body weight every day, every two days or every three days or within the range of 1-10 mg/kg every day, every two days or every three days.

Toxicity. Preferably, an effective amount (e.g., dose) of CXCR3 agonist or antagonist described herein will provide therapeutic benefit without causing substantial toxicity to the subject. Toxicity of the CXCR3 agonist or antagonist described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the CXCR3 agonist or antagonist described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

One or more suitable unit dosage forms may optionally be formulated for sustained release (for example using microencapsulation, see WO 94/07529, and U.S. Pat. No. 4,962,091), can be administered by a variety of routes including parenteral, including by intravenous and intramuscular routes. For example, the vaccine may be directly injected into a tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the compositions are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable carrier" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents can be prepared by procedures known in the art using well-known and readily available ingredients. The therapeutic agents can also be formulated as solutions appropriate for parenteral administration, for instance by intramuscular, subcutaneous or intravenous routes. The pharmaceutical formulations of the therapeutic agents can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition may be delivered via various routes and to various sites in an mammal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular subject.

Formulations of Pharmaceutical Compositions. The CXCR3 agonist or antagonist can be incorporated into pharmaceutical compositions suitable for administration. The pharmaceutical compositions generally comprise recombinant or substantially purified CXCR3 agonist or antagonist and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the polypeptide and antibody compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

Examples of carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the CXCR3 agonist or antagonist, use thereof in the compositions is contemplated. Supplementary active compounds can also be incorporated into the compositions.

A pharmaceutical composition of the invention is formulated to be compatible with its intended route of administration. The CXCR3 agonist or antagonist polypeptides compositions of the present invention can be administered by parenteral, topical, intravenous, oral, subcutaneous, intra-arterial, intradermal, transdermal, rectal, intracranial, intraperitoneal, intranasal; intramuscular route or as inhalants.

Methods of Preparing Antagonistic Antibodies

General Overview. Initially, a target polypeptide is chosen to which a binding agent (e.g., anti-CXCR3, anti-CXCL9, anti-CXCL10, or anti-CXCL11 antibody) can be raised. Techniques for generating binding agents directed to target polypeptides are well known to those skilled in the art. Examples of such techniques include, e.g., but are not limited to, those involving display libraries, xeno or human mice, hybridomas, and the like. Target polypeptides within the scope of the present invention include any polypeptide or polypeptide derivative which is capable of exhibiting antigenicity. Examples include, but are not limited to CXCR3, CXCL9, CXCL10, CXCL11 peptides, polypeptides, and fragments thereof.

It should be understood that not only are naturally-occurring antibodies suitable as binding agents for use in accordance with the present disclosure, but recombinantly engineered antibodies and antibody fragments, e.g., antibody-related polypeptides, which are directed to the target polypeptide and fragments thereof are also suitable.

Binding agents, e.g., anti-CXCR3, anti-CXCL9, anti-CXCL10, or anti-CXCL11 antibodies, that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

In suitable embodiments, binding agents are anti-CXCR3, anti-CXCL9, anti-CXCL10, or anti-CXCL11. Phage or phagemid display technologies are useful techniques to derive the binding agents of the present invention. Anti-CXCR3, anti-CXCL9, anti-CXCL10, or anti-CXCL11 antibodies useful in the present invention are "human antibodies," (e.g., antibodies isolated from a human) or "human sequence antibodies." Human antibodies can be made by a variety of methods known in the art including phage display methods. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741. Methods useful for the identification of nucleic acid sequences encoding members of multimeric polypeptide complex by screening polyphage particles have been described. Rudert et al., U.S. Pat. No. 6,667,150. Also, recombinant immunoglobulins can be produced. Cabilly, U.S. Pat. No. 4,816,567; Cabilly et al., U.S. Pat. No. 6,331, 415 and Queen et al., *Proc. Natl. Acad. Sci. USA* 86: 10029-10033, 1989. Techniques for generating and cloning monoclonal antibodies are well known to those skilled in the art. The anti-CXCR3, anti-CXCL9, anti-CXCL10, or anti-CXCL11 binding agents preferably have a high immunoreactivity, that is, percentages of antibodies molecules that are correctly folded so that they can specifically bind their target antigen. Expression of sequences encoding binding agents, e.g., antibodies of the invention, can be carried out in *E. coli* as described below. Such expression usually results in immunoreactivity of at least 80%, 90%, 95% or 99%.

Preparation of Polyclonal Antisera and Immunogens. Methods of Generating antibodies or antibody fragments of the invention typically include immunizing a subject (generally a non-human subject such as a mouse or rabbit) with a purified target polypeptide or homolog or fragment thereof or with a cell expressing the target polypeptide or homolog or fragment thereof. Any immunogenic portion of the target polypeptide can be employed as the immunogen. An appropriate immunogenic preparation can contain, e.g., a recombinantly-expressed CXCR3, CXCL9, CXCL10, or CXCL11 polypeptide or a chemically-synthesized CXCR3, CXCL9, CXCL10, or CXCL11 polypeptide. An isolated CXCR3, CXCL9, CXCL10, or CXCL11 polypeptide typically comprises at least four amino acid residues, and encompasses an epitope of the CXCR3, CXCL9, CXCL10, or CXCL11 polypeptide such that an antibody raised against the peptide forms a specific immune complex with the CXCR3, CXCL9, CXCL10, or CXCL11 polypeptide. Typically, the antigenic peptide comprises at least 5, 8, 10, 15, 20, or 30 amino acid residues. Longer antigenic peptides are sometimes preferable over shorter antigenic peptides, depending on use and according to methods well known to those skilled in the art. Typically, the immunogen will be at least about 8 amino acid residues in length, and preferably at least about 10 residues in length. Multimers of a given epitope are sometimes more effective than a monomer.

If needed, the immunogenicity of the CXCR3, CXCL9, CXCL10, or CXCL11 polypeptide can be increased by fusion or conjugation to a hapten such as keyhole limpet hemocyanin (KLH) or ovalbumin (OVA). Many such haptens are known in the art. One can also combine the polypeptide with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

For convenience, immune responses are often described in the present invention as being either "primary" or "secondary" immune responses. A primary immune response, which is also described as a "protective" immune response, refers to an immune response produced in an individual as a result of some initial exposure (e.g., the initial "immunization") to a particular antigen. Such an immunization can occur, e.g., as the result of some natural exposure to the antigen (e.g., from initial infection by some pathogen that exhibits or presents the antigen) or from antigen presented by cancer cells of some tumor in the individual (e.g., malignant melanoma). Alternatively, the immunization can occur as a result of vaccinating the individual with a vaccine containing the antigen. For example, the vaccine can be a vaccine comprising one or more antigens from a CXCR3, CXCL9, CXCL10, or CXCL11 polypeptide.

A primary immune response can become weakened or attenuated over time and can even disappear or at least become so attenuated that it cannot be detected. Accordingly, the present invention also relates to a "secondary" immune response, which is also described here as a "memory immune response." The term secondary immune response refers to an immune response elicited in an individual after a primary immune response has already been produced.

Thus, a secondary or immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4' cells. A first exposure to an antigen primes the immune system and additional exposure(s) results in a DTH.

Following appropriate immunization, the binding agent, e.g., anti-CXCR3, anti-CXCL9, anti-CXCL10, or anti-CXCL11 polyclonal antibody can be prepared from the subject's serum. If desired, the antibody molecules directed against the target polypeptide can be isolated from the mammal (e.g., from the blood) and further purified by well known techniques, such as polypeptide A chromatography to obtain the IgG fraction.

Monoclonal Antibody. In one embodiment, the binding agent is an anti-CXCR3, anti-CXCL9, anti-CXCL10, or anti-CXCL11 monoclonal antibody. For example, in some embodiments, the monoclonal antibody may be a human or a mouse monoclonal antibody. For preparation of monoclonal antibodies directed towards a particular target polypeptide, or derivatives, fragments, analogs or homologs thereof, any technique that provides for the production of antibody molecules by continuous cell line culture can be utilized. Such techniques include, but are not limited to, the hybridoma technique (see, e.g., Kohler & Milstein, 1975. *Nature* 256: 495-497); the trioma technique; the human B-cell hybridoma technique (see, e.g., Kozbor, et al., 1983. *Immunol. Today* 4: 72) and the EBV hybridoma technique to produce human monoclonal antibodies (see, e.g., Cole, et al., 1985. In: MONOCLONAL ANTIBODIES AND CANCER THERAPY, Alan R. Liss, Inc., pp. 77-96). Human monoclonal antibodies can be utilized in the practice of the invention and can be produced by using human hybridomas (see, e.g., Cote, et al., 1983. *Proc. Natl. Acad. Sci. USA* 80: 2026-2030) or by transforming human B-cells with Epstein Barr Virus in vitro (see, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the target polypeptide. Alternatively, hybridomas expressing monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., target polypeptide binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added a reactive amino acid side chains, e.g., lysine to enhance the immunogenic properties of the target polypeptide. Also, CPG-dinucleotide technique can be used to enhance the immunogenic properties of the target polypeptide. Other manipulations include substituting or deleting particular amino acyl residues that contribute to instability of the antibody during storage or after administration to a subject, and affinity maturation techniques to improve affinity of the antibody of the target polypeptide.

Hybridoma Technique. In one embodiment, the binding agent is a monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, N.Y., 349 (1988); Hammerling et al., *Monoclonal Antibodies And T-Cell Hybridomas*, 563-681 (1981). Other methods for producing hybridomas and monoclonal antibodies are well known to those of skill in the art.

Phage Display Technique. As noted above, the binding agents can be produced through the application of recombinant DNA and phage display technology. For example, binding agents of the invention, e.g., anti-CXCR3, anti-CXCL9, anti-CXCL10, or anti-CXCL11 antibodies, can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g., human or murine) by selecting directly with antigen, typically antigen bound or captured to a solid surface or bead. Phage used in these methods are typically filamentous phage including fd and M13 with Fab, Fv or disulfide stabilized Fv antibody domains are recombinantly fused to either the phage gene III or gene VIII protein. In addition, methods can be adapted for the construction of Fab expression libraries (see, e.g., Huse, et al., *Science* 246: 1275-1281, 1989) to allow rapid and effective identification of monoclonal Fab fragments with the desired specificity for a target polypeptide, e.g., a polypeptide or derivatives, fragments, analogs or homologs thereof. Other examples of phage display methods that can be used to make the binding agents of the present invention include those disclosed in Huston et al., *Proc. Natl. Acad. Sci. U.S.A.*, 85: 5879-5883, 1988; Chaudhary et al., *Proc. Natl. Acad. Sci. U.S.A.*, 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Binding Agents. As noted above, the binding agents can be produced through the application of recombinant DNA technology. Recombinant polynucleotide constructs encoding a binding agent typically include an expression control sequence operably-linked to the coding sequences of antibody chains, including naturally-associated or heterologous promoter regions. As such, another aspect includes vectors containing one or more nucleic acid sequences encoding a binding agent. For recombinant expression of one or more the polypeptides, the nucleic acid containing all or a portion of the nucleotide sequence encoding the binding agent is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160; 6,680,192.

Single Chain Antibodies. In one embodiment, the binding agent is a single chain anti-CXCR3, anti-CXCL9, anti-CXCL10, or anti-CXCL11 antibody. According to the invention, techniques can be adapted for the production of single-chain antibodies specific to a CXCR3, CXCL9, CXCL10, or CXCL11 polypeptide (see, e.g., U.S. Pat. No. 4,946,778). Examples of techniques which can be used to produce single-chain Fvs and antibodies of the invention include those described in U.S. Pat. Nos. 4,946,778 and 5,258,498; Huston et al., *Methods in Enzymology,* 203: 46-88, 1991; Shu, L. et al., *Proc. Natl. Acad. Sci. USA,* 90: 7995-7999, 1993; and Skerra et al., *Science* 240: 1038-1040, 1988.

Chimeric and Humanized Antibodies. In one embodiment, the binding agent is a chimeric anti-CXCR3, anti-CXCL9, anti-CXCL10, or anti-CXCL11 antibody. In one embodiment, the binding agent is a humanized anti-CXCR3, anti-CXCL9, anti-CXCL10, or anti-CXCL11 antibody. In one embodiment, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-CXCR3, anti-CXCL9, anti-CXCL10, or anti-CXCL11 antibodies, such as chimeric and humanized monoclonal antibodies, comprising both human and non-human portions, can be made using standard recombinant DNA techniques, and are within the scope of the invention. For some uses, including in vivo use of the binding agent of the invention in humans as well as use of these agents in vitro detection assays, it is preferable to use chimeric, humanized, or human antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187, European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. Cancer Res. 47: 999-1005; Wood, et al., 1985. *Nature* 314: 446-449; Shaw, et al., 1988. *J. Natl. Cancer Inst.* 80: 1553-1559); Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., *Molecular Immunology,* 28: 489-498, 1991; Studnicka et al., *Protein Engineering* 7: 805-814, 1994; Roguska et al., *PNAS* 91: 969-973, 1994), and chain shuffling (U.S. Pat. No. 5,565,332). In one embodiment, a cDNA encoding a murine monoclonal antibody is digested with a restriction enzyme selected specifically to remove the sequence encoding the Fc constant region, and the equivalent portion of a cDNA encoding a human Fc constant region is substituted (see Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) Science 240: 1041-1043; Liu et al. (1987) *Proc. Natl. Acad. Sci. USA* 84: 3439-3443; Liu et al. (1987) *J Immunol* 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559); U.S. Pat. No. 6,180,370; U.S. Pat. Nos. 6,300,064; 6,696,248; 6,706,484; 6,828,422.

In one embodiment, the present invention allows the construction of humanized antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present invention provides for a humanized antibodies, heavy and light chain immunoglobulins.

CDR Antibodies. In one embodiment, the binding agent is a CDR antibody. Generally the donor and acceptor antibodies used to generate the CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently all three CDRs in all variable domains of the acceptor antibody will be replaced with the corresponding donor CDRs, though one need replace only as many as necessary to permit adequate binding of the resulting CDR-grafted antibody to MetAp3. Methods for generating CDR-grafted and humanized antibodies are taught by Queen et al. U.S. Pat. No. 5,585,089, U.S. Pat. No. 5,693,761; U.S. Pat. No. 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting CDR grafted antibody by replacing certain residues of a given FR to make the FR more similar to the corresponding FR of the donor antibody. Preferred locations of the substitutions include amino acid residues adjacent to the CDR, or which are capable of interacting with a CDR (see, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified CDR antibody significantly compared to the same antibody with a fully human FR.

Fusion Proteins. In one embodiment, the binding agent is a fusion protein. The binding agents, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present invention can also be engineered to improve characteristics of the binding agent. For instance, a region of additional amino acids, particularly charged amino acids, can be added to the N-terminus of the binding agent to improve stability and persistence during purification from the host cell or subsequent handling and storage. Also, peptide moieties can be added to the binding agent to facilitate purification. Such regions can be removed prior to final preparation of the binding agent. The addition of peptide moieties to facilitate handling of polypeptides are familiar and routine techniques in the art. The binding agent can be fused to marker sequences, such as a peptide which facilitates purification of the fused polypeptide. In some embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusions can be engineered using the polynucleotides or the polypeptides of the present invention. Also, the fusion protein can show an increased half-life in vivo.

Fusion proteins having disulfide-linked dimeric structures (due to the IgG) can be more efficient in binding and neutralizing other molecules, than the monomeric secreted protein or protein fragment alone. Fountoulakis et al., *J. Biochem.* 270: 3958-3964, 1995.

Similarly, EP-A-0 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, e.g., improved pharmacokinetic properties. See EP-A 0232 262. Alternatively, deleting the Fc part after the fusion protein has been expressed, detected, and purified, would be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5 Bennett et al., *J. Molecular Recognition* 8: 52-58, 1995; Johanson et al., *J. Biol. Chem.*, 270: 9459-9471, 1995.

Methods for identifying and/or screening the binding agents. Methods useful to identify and screen the binding agents, e.g., anti-CXCR3, anti-CXCL9, anti-CXCL10, or anti-CXCL11 antibodies and antibody-related polypeptides, that possess the desired specificity to the target polypeptide include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A; et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS*, 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood*, 72: 1310-5, 1988); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in PBMCs can be measured by placing PMBCs in wells together with labeled particles (Peters et al., *Blood*, 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, binding agents are selected using display of candidate binding agents on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. No. 5,871,907; U.S. Pat. No. 5,969,108; U.S. Pat. No. 6,225,447; U.S. Pat. No. 6,291,650; U.S. Pat. No. 6,492,160.

In one embodiment, binding agents are selected using display of candidate binding agents on the surface of a yeast host cell. Methods useful for the isolation of scFv polypeptides by yeast surface display have been described by Kieke et al., *Protein Eng.* 1997 November; 10(11): 1303-10.

In one embodiment, binding agents are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In one embodiment, binding agents are selected using tRNA display of candidate binding agents. Methods useful for in vitro selection of ligands using tRNA display have been described by Merryman et al., *Chem. Biol.*, 9: 741-46, 2002.

In one embodiment, binding agents are selected using RNA display. Methods useful for selecting peptides and proteins using RNA display libraries have been described by Roberts et al. *Proc. Natl. Acad. Sci. USA*, 94: 12297-302, 1997; and Nemoto et al., *FEBS Lett.*, 414: 405-8, 1997. Methods useful for selecting peptides and proteins using unnatural RNA display libraries have been described by Frankel et al., *Curr. Opin. Struct. Biol.*, 13: 506-12, 2003.

In one embodiment, binding agents are expressed in the periplasm of gram negative bacteria and mixed with labeled target polypeptide. See WO 02/34886. In clones expressing recombinant polypeptides with affinity for the target polypeptide, the concentration of the labeled target polypeptide bound to the binding agents is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired binding agent, it is contemplated that it can be produced in large volume by any technique known to those skilled in the art, e.g., prokaryotic or eukaryotic cell expression and the like. The binding agents which are, e.g., but not limited to, anti-CXCR3, anti-CXCL9, anti-CXCL10, or anti-CXCL11 hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Experimental Animal Models

The methods and compositions described herein have beneficial effects on myelogenesis especially in the context of chemotherapy. Various models exist, both in vivo (in animals and humans) and in vitro, that allow certain aspects of the process of myelogenesis to be investigated. Such models can be used to study the effectiveness of the compositions and methods of the invention, and, for example, to select a dosage or administration protocol. For example, the level or proliferative activity of bone marrow stem cells or bone marrow progenitor cells can be determined either in bone marrow or in circulating blood. Progenitor cells such as CFU-GM, CFU-GEMM, BFU-E, or CFU-S can be isolated from mice or humans, their numbers counted, and the cells cultured to ascertain the effectiveness of a composition or method of the invention in stimulating bone marrow regeneration of the progenitor cell donor. Alternatively, a competitive regeneration assay can be performed, in which the repopulating ability of a test marrow specimen is evaluated in lethally irradiated mice. In vitro colony assays, such as the CFU-GM, BFU-E, CFU-GEMM, and CFu-Blast assays, also can be employed to measure the number of healthy stem cells in a sample from a treated animal or human. Further examples of such assays can be found in Mauch et al., *Int. J. Radiation*, 31:1319-1339 (1995).

One aspect of the invention is a method for treating cancer. One such method includes administering to a cancer patient a CXCR3 agonist prior to administering chemotherapy or radiation therapy. Another such method includes administering a CXCR3 antagonist after administering chemotherapy or radiation therapy. A number of animal models of cancer are known which can be used to select an appropriate dose or administration protocol for carrying out a method or using a composition of the invention.

Colon adenocarcinoma in rodents induced by the procarcinogen 1,2-dimethylhydrazine and its metabolite azoxymethane (AOM) is a well-characterized carcinogen-induced tumor because of its morphological similarity to human colon cancer, high reproducibility and relatively short latency period (Shamsuddin, *Human Path.*, 17:451-153 (1986)). This rodent tumor model is similar to human colon adenocarcinoma not only in its morphology (Shamsuddin & Trump, *J. Natl. Cancer Inst.*, 66:389-401 (1981)), but also in the genes that are involved in tumorigenesis (Shivapurkar et al., *Cancer Lett.*, 96:63-70 (1995); Takahashi et al., *Carcinogenesis*, 21:1117-1120 (2000)).

In addition to chemical carcinogen-induced models of colon cancer in rodents, gene disruption of the catalytic subunits of phosphoinositide-3-OH kinase (PI3-Ky) (Sasaki et al., *Nature*, 406:897-902 (2000)) or the guanosine-binding protein Gai2 (Rudolph et al., *Nat. Genet.*, 10:143-50 (1995)) causes spontaneous colon cancer in rodents. These studies indicate that potential causes other than alterations in the prototypical tumor suppressor genes and oncogenes could be involved in the etiology of human colon cancer.

A number of animal models for oral squamous cell carcinoma have been developed, including rat, mouse and hamster models. A hamster cheek pouch tumor model induced by the carcinogen 7,12-dimethylbenzanthracene remains one of the most common models (Baker (1986) Malignant neoplasms of the oral cavity. *In: Otolaryngology-Head and Neck Surgery*, Cummings et al. (eds.) 1281-1343. St. Louis, Mo.: CV Mosby), but exhibits a number of differences from human oral cavity tumorigenesis. A recent mouse model using the carcinogen 4-nitroquinoline 1-oxide (4-NQO) has been developed which more closely simulates many aspects of human oral cavity and esophageal carcinogenesis (Tang et al., *Clin. Cancer Res.*, 10:301-313 (2004)).

An animal model for multiple myeloma has been described (Garrett et al., *Bone*, 20:515-520 (1997)), which uses a murine myeloma cell line 5TGM1 that causes lesions characteristic of human myeloma when injected into mice. Such lesions include severe osteolysis and the involvement of non-bone organs including liver and kidney. Mice inoculated with cultured 5TGM1 cells predictably and reproducibly develop disease, symptoms of which include the formation of a monoclonal gammopathy and radiologic bone lesions.

A number of animal models for the study of glioma exist, including an intracerebral rat glioma model (Sandstrom et al., *Br. J. Cancer,* 91:1174-1180 (2004)), and a murine model using injection of dog-derived J3T1 glioma cells (U.S. Pat. No. 6,677,155).

Animal models for the study of non-small cell lung cancer have been previously described, for example, by xenografting human tumors by subcutaneous transplantation of LC-6 human non-small cell lung cancer into BALB/C-nu/nu mice (Tashiro et al., *Cancer Chemother. Pharmacol.*, 24:187 (1989)).

An animal model for the study of stomach cancer has been described which uses AZ-521 human stomach cancer xenografts in nude mice (Fukushima et. al., *Biochem. Pharmacol.*, 59:1227-1236 (2000)).

Numerous animal models of AML have been previously described, including in rats (Blatt, J et al., *Leuk. Res.,* 15:391-394 (1991)), and SCID mice (Vey, N. et al., *Clin. Cancer Res.,* 6:731-736 (2000)).

A number of animal models used for the study of HCC have been described (Chisari et al., *Science,* 230:1157-1160 (1985); Babinet et al., *Science,* 230:1160-1180; U.S. Publication No. 2004/0016011). These references disclose the generation of transgenic mouse models of HCC by incorporating the HBV virus into the genome.

Animal models with experimental metastasis pattern resembling those frequently observed in human patients (Engebraaten & Fodstad, *Int. J. Cancer,* 82:219-25 (1999)), which use MA-11 and MT-1, two estrogen and progesterone receptor-negative human breast cancer cell lines. Other models for breast cancer include U.S. Publication No. 2003/0215861 (herein incorporated by reference). Alternatively, the ability of the compounds of the present invention to function as anti-breast cancer agents, either alone or in combination with other agents, can be demonstrated in vivo in carcinogen induced mammary tumors in wild type Sprague-Dawley Rats (Thompson H. J et al., *Carcinogenesis,* 13:1535-1539 (1992)).

A number of animal models for ovarian cancer are known in the art. For example, Connolly et al., *Cancer Research,* 63:1389-1397 (2003), discloses methods of developing epithelial ovarian cancer in mice by chimeric expression of the SV40 Tag under control of the MISIIR promoter. In another example, Liu et al., *Cancer Research,* 64:1655-1663 (2004), have introduced human HRAS or KRAS oncogenes into immortalized human ovarian surface epithelial cells, which form subcutaneous tumors after injection into immunocompromised mice.

Numerous animal models for the study of prostate cancer are available. One murine model, using prostate cancer xenografts introduced into SCID mice, is disclosed in U.S. Pat. No. 6,756,036. Alternatively, an orthotopic mouse model of metastatic prostate cancer can be used, as disclosed in U.S. Publication No. 2004/0009508.

EXAMPLES

The present invention is further illustrated by the following examples, which should not be construed as limiting in any way.

The therapeutic utility of CXCR3 agonists and antagonists in myeloprotection and enhancing hematopoietic recovery was investigated in mice according to the procedures set forth in these Examples. Using the methods described below, it would also be possible for the skilled artisan to generate and/or compare additional CXCR3 agonists and antagonists to the ones shown in these examples.

Example 1

Radiation Induces Expression of CXCR3 Ligands and CXCR3

Figure 1B:
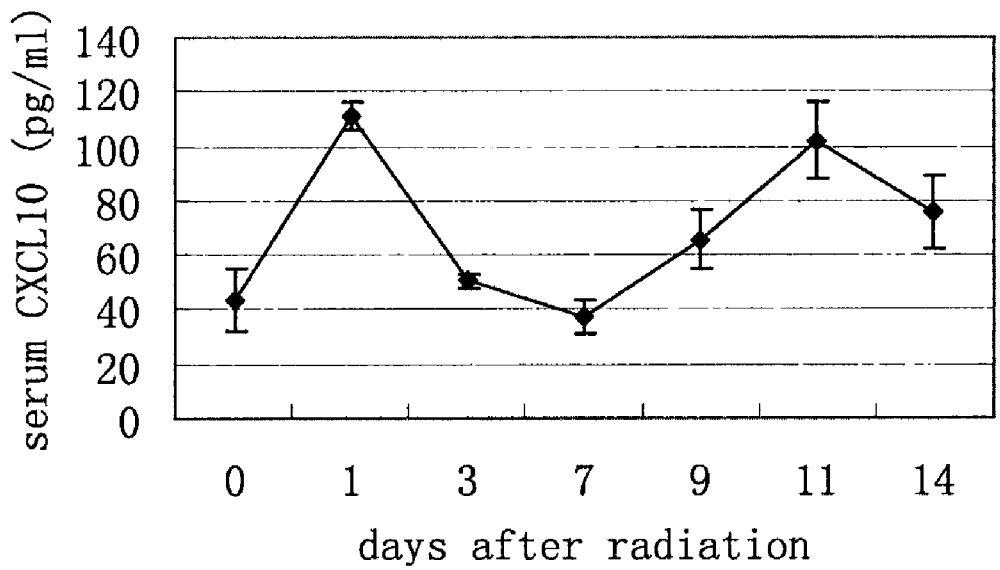
Figure 1C:
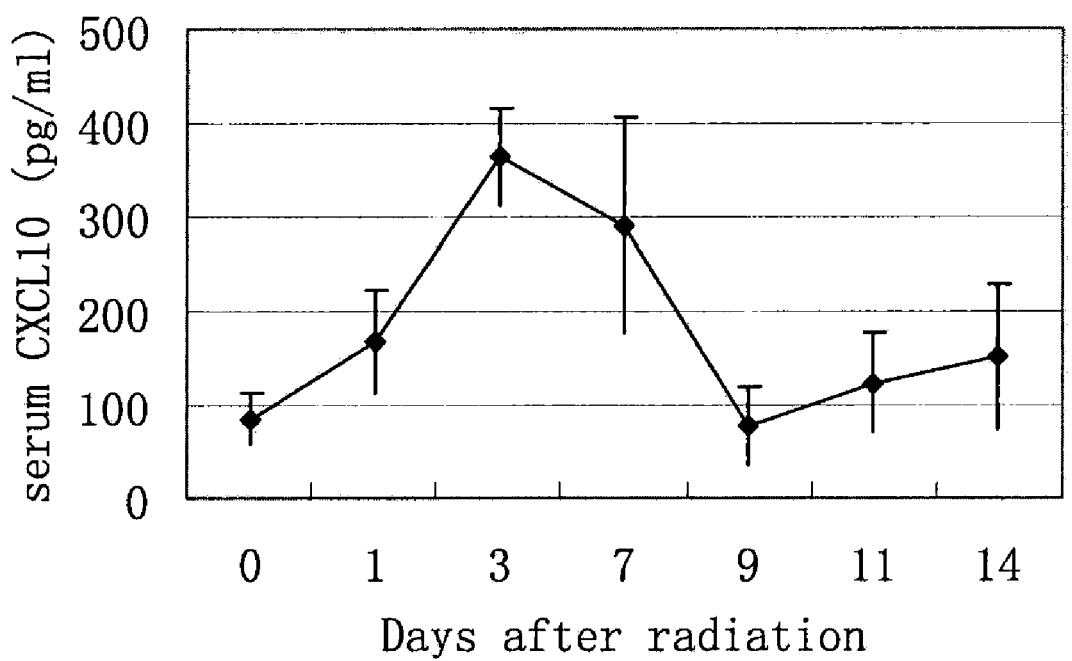

Female C57 mice approximately 9 weeks of age were irradiated by gamma rays of 353 cGy ($^{137}$Cs radiation source). The sera of mice were analyzed at days 0, 1, 3, 7, 9, 11, 14 post radiation for expression of CXCR3 ligands using a mouse CXCL9, CXCL10, and CXCL11 ELISA (R&D System). The levels of CXCL9, CXCL10, and CXCL11 are shown in FIGS. 1A, 1B, and 1C, respectively. The expression of all three ligands increased after radiation, although the increase in CXCL9 did not occur until about day 11 after radiation.

Figure 2:
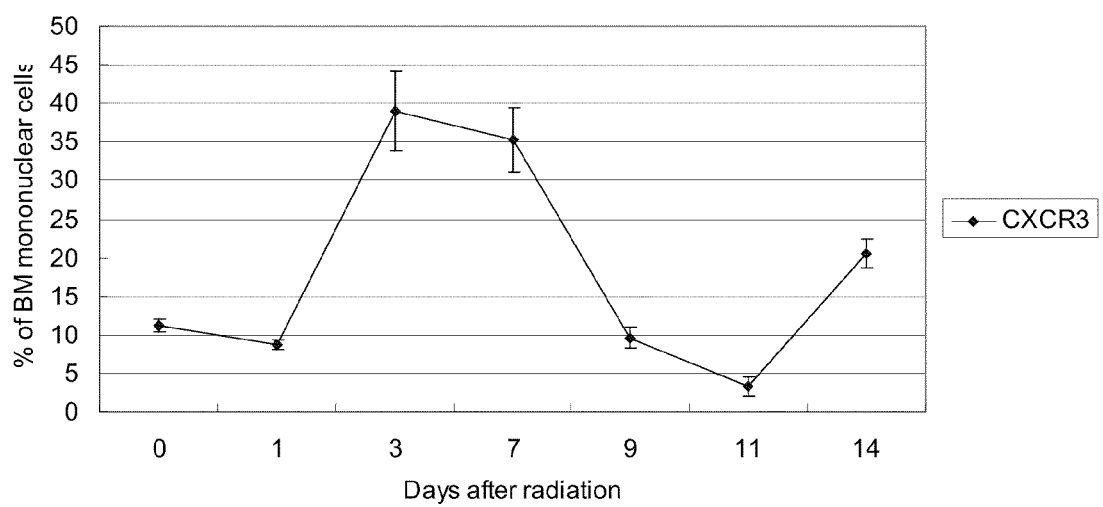
FIG. 2 shows a graph of the expression of CXCR3 receptor on BM mononuclear cells in mice after radiation treatment.

The expression of the CXCR3 receptor was investigated in BM mononuclear cells by flow cytometry using a commercial phycoerythrin (PE)-conjugated monoclonal anti-mouse CXCR3 (Pharmingen, San Diego, Calif., USA). The results are shown in FIG. 2 and indicate that CXCR3 was induced after radiation therapy in mice.

Example 2

Chemotherapy Induces Expression of CXCR3 Ligands and CXCR3

Figure 6A:
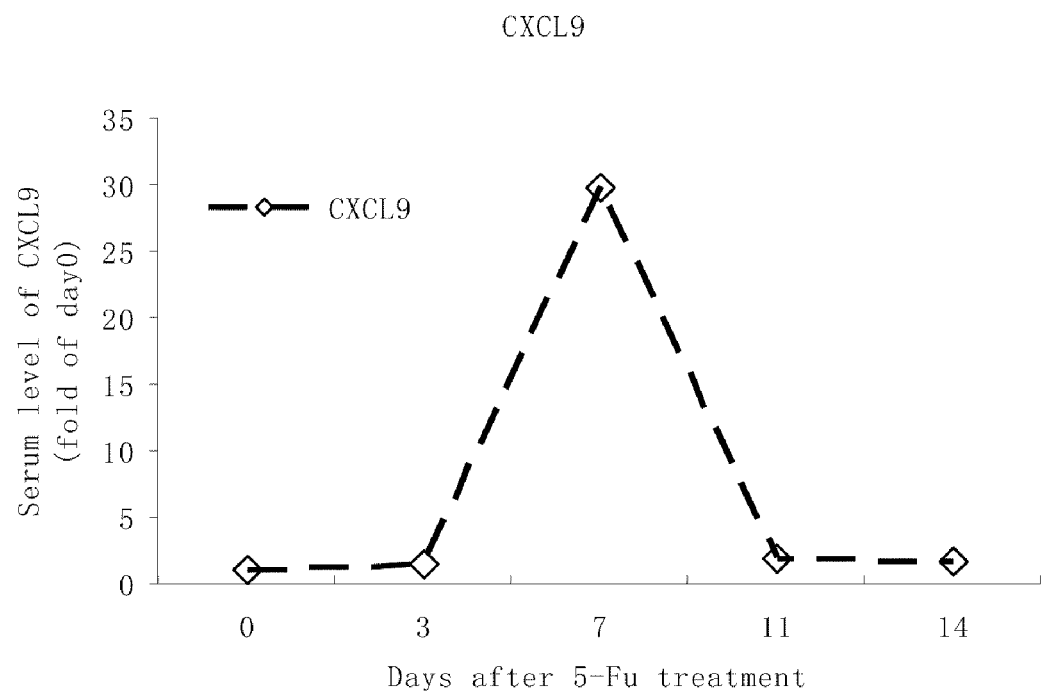
FIGS. 6A-6D show graphs of the expression of CXCL9, CXCL10, and CXCL11, and CXCR3, respectively, after 5-FU treatment.
Figure 6B:
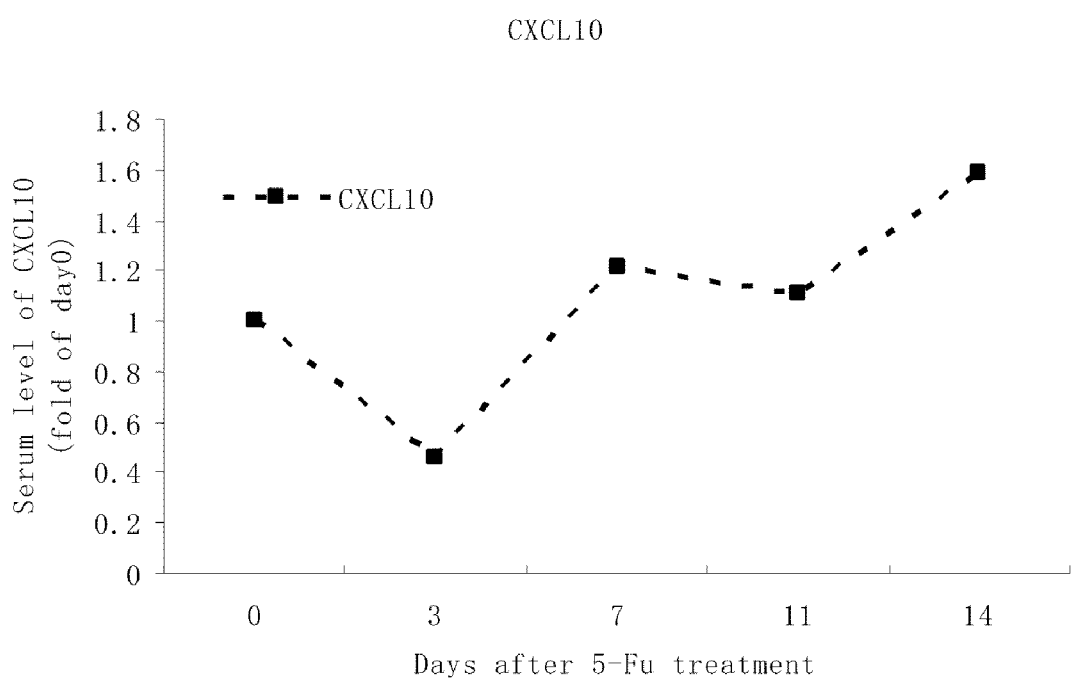
Figure 6C:
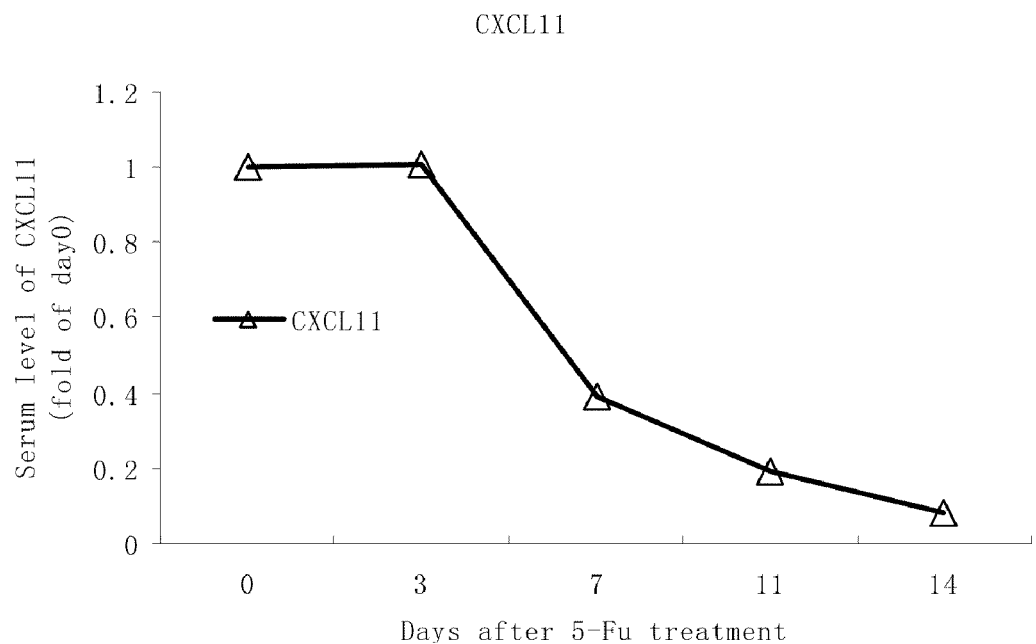
Figure 6D:
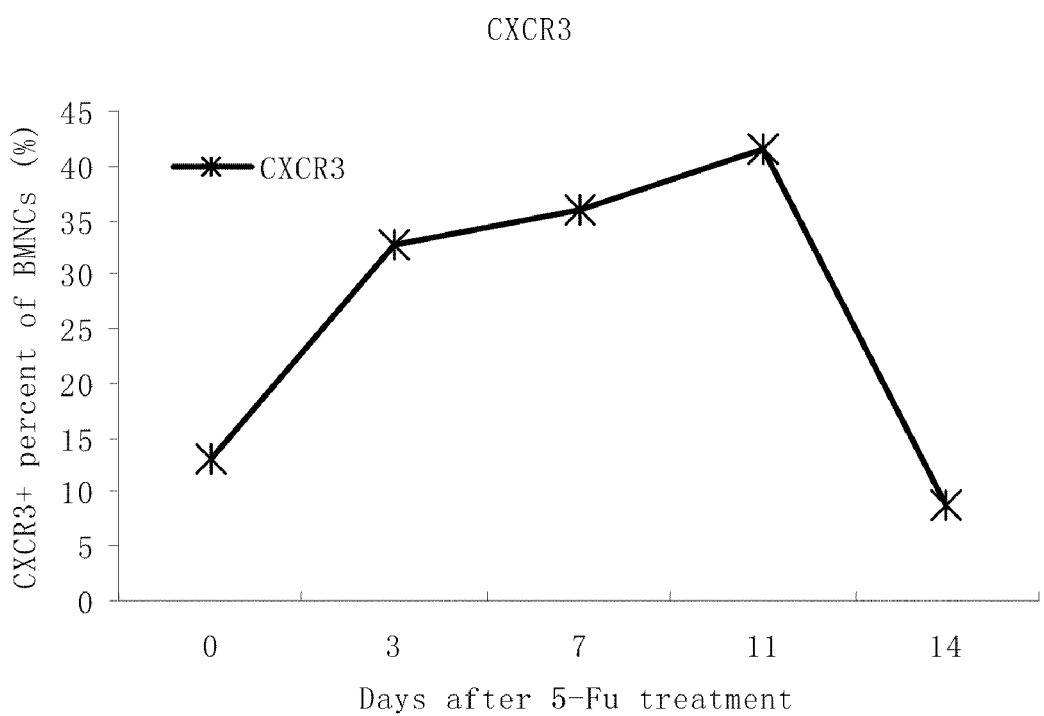
Figure 7:
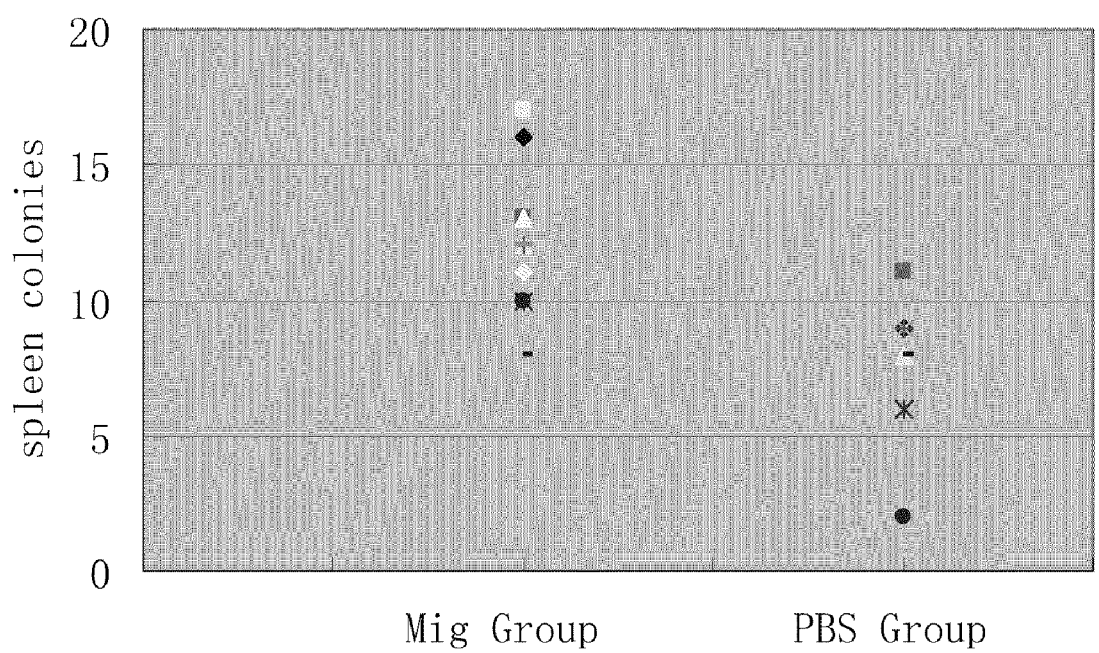
FIG. 7 is a graph showing that recombinant CXCL9 protects the murine hematopoietic stem cells from the damage by the chemotherapeutic agent Ara-C.

8-week-old male C57BL/6 mice were injected 250 mg/kg 5-FU through tail-vein. Serum levels of CXCL9 (Mig), CXCL10, CXCL11 were measured by commercial ELISA kit (FIG. 6A-6C). Expression of CXCR3 in BM cells were analyzed by flow cytometry using commercial anti-CXCR3 monoclonal antibody conjugated with FITC (FIG. 6D).

Example 3

Administration of Anti-CXCL9 Antibodies After Radiation Therapy Accelerated BM Recovery Anti-MuCXCL9 polyclonal antibodies were raised in Wistar rats (SLAC) using purified rMuCXCL9. Briefly, 300 μg of rMUCXCL9 was mixed with equal volume of Freund's complete adjuvant and injected subcutaneously into the rats. From the 21$^{st}$ day after the first injection, rats were boosted by injection of the proteins mixed with equal volume of Freund's incomplete adjuvant every week for 3 weeks. Antibodies were collected from the animals two weeks after the last booster.

Anti-CXCL9 and control sera were administered to mice at the same time as they received a dose of radiation. The day of the radiation treatment was considered as day 0, and the sera were administered consecutively from day 0 to day 10, once per day. Immediately before injection, 1 μl of the serum was obtained and diluted with normal saline to 10 μl. As described for the ELISA experiments above, CXCL9 levels are up-regulated after radiation treatment.

Blood samples were obtained by puncture of the eye vein and white blood cells and platelets were counted automatically on a hematology analyzer (MEK6300, Japan). Peripheral blood counts are depicted as average values plus or minus SEM. To obtain bone marrow samples, mice were killed by cervical dislocation after isoflurane anesthesia. Bone marrow cells were harvested by flushing two femur and tibia bones with IMDM medium.

Peripheral blood samples were obtained by retro-orbital bleeding of 1 mL peripheral blood. Each blood sample was coagulated in the refrigerator at 4° C. and centrifuged at 1000×g for 15 min. The serum was collected and stored at −70° C. Aliquots were used once only and were not subjected to repeated freeze-thaw cycles.

Bone marrow mononuclear cells were isolated from mouse femurs by Ficoll gradient centrifugation. Briefly, the cells were fixed in 50% ethanol 1 h before FACS. The cells were centrifuged and resuspended in 0.4 ml of PBS, 5 mM EDTA containing 20 μg RNaseA and 20 μg propidium iodide (PI) (Sino-American Biotec, Beijing, China). G1, G2 and S phases of the cell cycle were analyzed using the FACS Calibur flow cytometer (Becton Dickinson, USA). Results were statistically analyzed using a Student t test or one-way ANOVA analysis. The results are expressed as mean value plus or minus standard error of the mean (SEM).

Figure 3A:
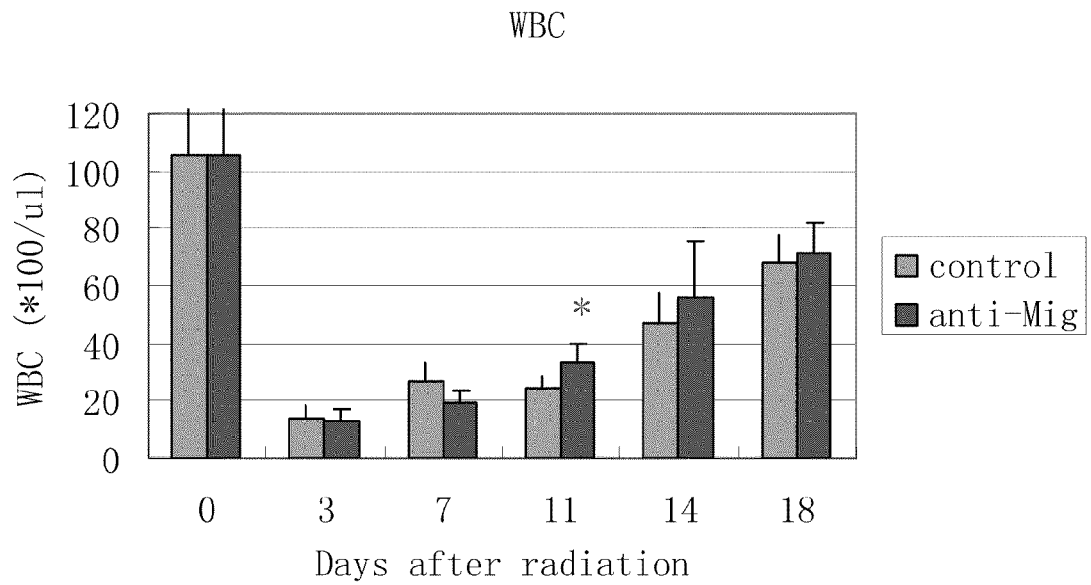
FIG. 3 shows graphs of hematological blood cell indices—WBC (FIG. 3A), platelets (FIG. 3B), and bone marrow cells (FIG. 3C)—in mice which were administered polyclonal anti-CXCL9 serum after radiation treatment.
Figure 3B:
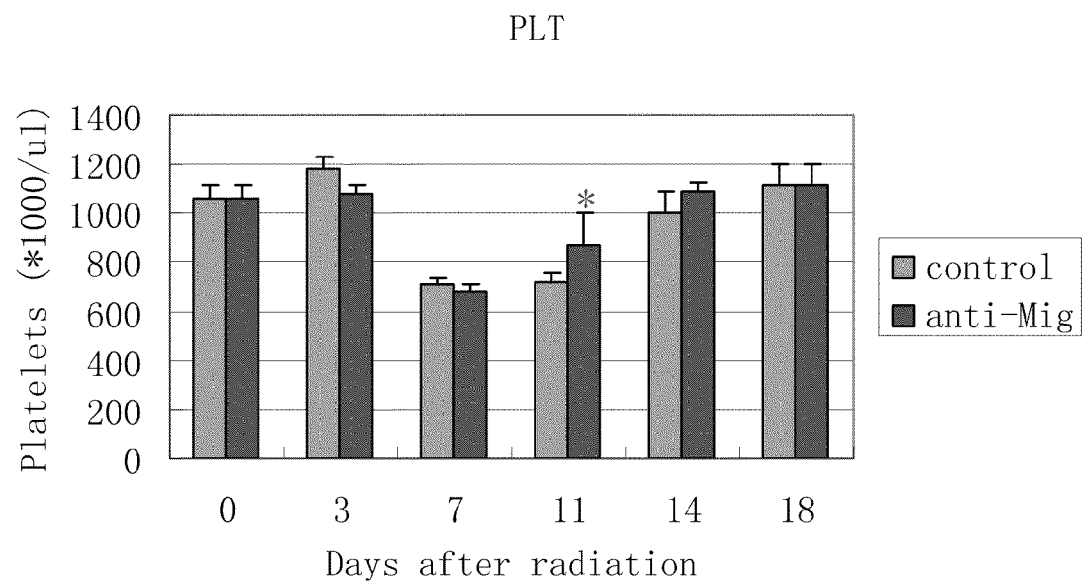

FIGS. 3A and 3B shows the white blood cell and platelet counts, respectively, from 1 µl of peripheral blood. There was no significant difference between the control serum and the anti-CXCL9 serum groups from day 0 to 7. At day 11, the mice of the anti-CXCL9 serum group recovered better than the control group, as indicated by *.

Figure 3C:
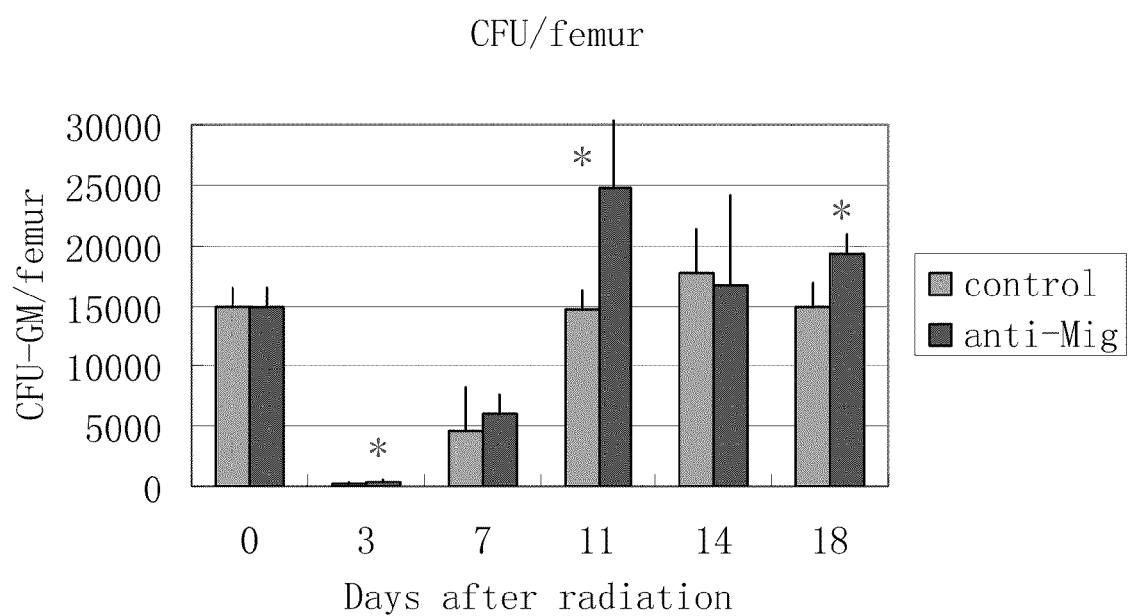

FIG. 3C shows the bone marrow cell counts from one femur. The anti-CXCL9 serum group recovered better than the control group as indicated by the *. Significance of the differences between groups was calculated by one-way ANOVA and p*<0.01. Accordingly, a CXCR3 antagonist (CXCL9 antiserum) is useful in methods of enhancing hematopoietic recovery when administered to subjects following radiation therapy.

Example 4

Administration of Anti-CXCL10 and Anti-CXCL11 Antibodies after Radiation Therapy Accelerates BM Recovery (Prophetic)

Anti-MuCXCL10 and anti-MuCXCL11 polyclonal antibodies are raised in Wistar rats (SLAC) using purified rMuCXCL10 and rMuCXCL11, respectively. Briefly, 300 µg of rMuCXCL10 and rMuCXCL11 are mixed with equal volume of Freund's complete adjuvant and injected subcutaneously into the rats. From the $21^{st}$ day after the first injection, rats are boosted by injection of the proteins mixed with equal volume of Freund's incomplete adjuvant every week for 3 weeks. Antibodies are collected from the animals two weeks after the last booster.

Anti-MuCXCL10, anti-MuCXCL11 and control sera are administered to mice at the same time as they received a dose of radiation. The day of the radiation treatment is considered as day 0, and the sera are administered consecutively from day 0 to day 10, once per day. Immediately before injection, 1 µl of the serum is obtained and diluted with normal saline to 10 µl. As described for the ELISA experiments above, CXCL10 and CXCL11 levels are up-regulated after radiation treatment.

Blood samples are obtained as described in Example 3. The results of the treatment groups are compared to a control not administered the CXCR3 antagonistic antibody. The results may be interpreted as having a beneficial effect on hematopoietic recovery when the hematological blood cell indices are increased following chemotherapy for mice administered the anti-MuCXCL10 and/or anti-MuCXCL11 compared to mice administered the control sera.

Example 5

Administration of CXCR3 Agonists Before Radiation Therapy Protects Against BM Damage (Prophetic)

The effect of rMuCXCL9, rMuCXCL10, and/or rMuCXCL11 on hematological blood cell indices of mice treated with radiation is investigated. rMuCXCL9, rMuCXCL10, and/or rMuCXCL11 are administered at 0.01 to 1 mg/kg once daily for 5 consecutive days. Next, the mice receive radiation by gamma rays of 353 cGy ($^{137}$Cs radiation source). Control mice are administered PBS. For each of several days following radiotherapy, mice are sacrificed by cervical dislocation. Hematological blood cell indices—peripheral WBC, platelets, and BMCs—are analyzed. The results of the treatment groups are compared to a control not administered the CXCR3 agonist therapy. The CXCR3 agonists may be interpreted as having a myeloprotective effect when the hematological blood cell indices are increased following radiation therapy for mice administered the agonists compared to mice not administered the agonists.

Example 6

CXCL9 Expression is Induced by CTX Chemotherapy

Specific pathogen-free BALB/c mice, at 8 weeks old, were purchased from Shanghai Laboratory Animal Center and quarantined for at least 7 days prior to use. Mice were maintained on commercial rodent food, given sterile water, and housed at approximately 23° C. and 55% relative humidity throughout the experiment.

Figure 4:
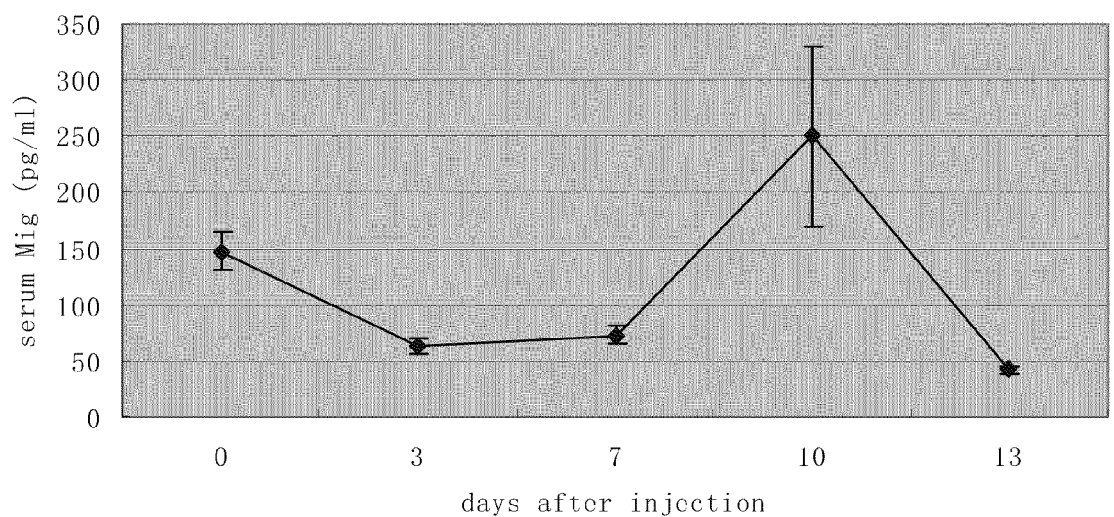
FIG. 4 shows a graph of the serum level of the CXCR3 ligand CXCL9 in mice after injection with cyclophosphamide (CTX).

Mice were injected with CTX (cyclophosphamide), a cell-cycle independent chemotherapeutic agent) intraperitoneally at a dosage of 300 mg/kg at day 0, Serum levels of CXCL9 were measured using commercial ELISA kits (n=4 for each time point). The level of CXCL9 is shown in FIG. 4 and shows a significant increase in expression at day 10.

Example 7

Figure 5:
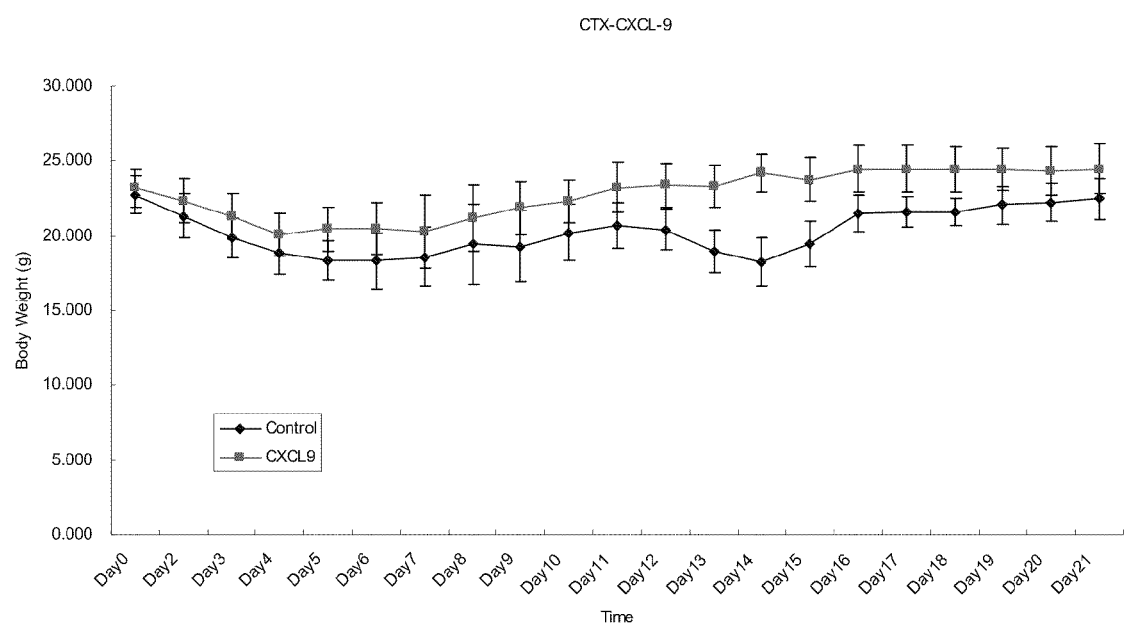
FIG. 5 shows a graph of the body weight of mice administered CTX chemotherapy after receiving pre-treatment with CXCL9 or a saline control.

Administration of CXCL9 Before CTX Chemotherapy Enhances Survival rMuCXCL9 was prepared as described in PCT/CN2007/000971 (filed Mar. 26, 2007). The effect of rMuCXCL9 on survival of mice treated with CTX was investigated. rMuCXCL9 was administered at 200 ng per mouse once daily for 5 consecutive days. Subsequently, the mice received CTX for 3 consecutive days at 100 mg/kg. The control group received saline before CTX treatment. The body weight of 13 mice of each group was measured (FIG. 5). The average body weight of the CXCL9 pre-treated group was significantly higher than that of the control (ANOVA, p<0.01). Accordingly, the administration of CXCR3 agonists, such as CXCL9, prior to cell cycle independent chemotherapy, is useful in methods for providing myeloprotection and enhancing survival.

Example 8

Administration of CXCR3 Antagonists After CTX Chemotherapy Accelerates BM Recovery (Prophetic)

Anti-MuCXCL9, anti-MuCXCL10, anti-MuCXCL11 (and combinations thereof), as well as control sera are administered to mice one to four hours after they receive a high dose of CTX (250 mg/kg). The day of the chemotherapy treatment is considered as day 0, and the sera are administered consecutively from day 0 to day 10, once per day. Immediately before injection, 1 µl of the serum is obtained and diluted with normal saline to 10 µl.

Blood samples are obtained as described in Example 2. The results of the treatment groups are compared to a control not administered the CXCR3 antagonistic antibody. The results may be interpreted as having a beneficial effect on hematopoietic recovery when the hematological blood cell indices are increased following chemotherapy for mice administered the anti-MuCXCL9, anti-MuCXCL10 and/or anti-MuCXCL11 compared to mice administered the control sera.

Example 9

Administration of CXCR3 Agonists CXCL10 and CXCL11 Before Chemotherapy Protects Against BM Damage (Prophetic)

The effect of rMuCXCL10 and/or rMuCXCL11 on hematological blood cell indices of mice treated with CTX is investigated. rMuCXCL10, and/or rMuCXCL11 are administered at 0.01 to 1 mg/kg once daily for 5 consecutive days. Next, the mice receive CTX for 3 consecutive days at 100 mg/kg or a single injection at 100 mg/kg. Control mice are administered PBS instead of rMuCXCL10, and/or rMuCXCL11. For each of several days following chemotherapy, mice are sacrificed by cervical dislocation. Hematological blood cell indices—peripheral WBC, platelets, and BMCs—are analyzed. The results of the treatment groups are compared to a control not administered the CXCR3 agonist therapy. The CXCR3 agonists may be interpreted as having a myeloprotective effect when the hematological blood cell indices are increased following CTX therapy for mice administered the agonists compared to mice not administered the agonists.

Example 10

Administration of CXCL9 to Hematopoietic Stem Cells Before Chemotherapy Protects Hematopoietic Stem Cells from Damage by the Chemotherapeutic Agent Ara-C The classic CFU-S assay was used to evaluate the number of hematopoietic stem cells (HSCs) in vivo after transplanting the in vitro treated bone marrow lineage-negative cells (BM Lin⁻ cells, enriched for HSCs). The recipient mice are lethally irradiated to deplete the endogenous HSCs. The engrafted HSCs are readout after 11 days of transplantation by counting the number of nodules of the recipient murine spleen. Each nodule represents a single engrafted HSC. BM Lin⁻ cells were isolated from 8-week-old C57BL/6 male mice using a commercial cell purification kit.

First, the purified cells were subjected to the culture at 37° C. for 4 hrs in the commercial medium of IMDM plus 20% fetal bovine serum (FBS) and supplemented with commercial recombinant factors including mouse c-kit ligand (mKL at 10 ng/ml), mouse interleukin-3 (mIL-3 at 10 ng/ml), mouse interleukin-6 at 10 ng/ml), human granulocyte colony stimulation factor (hG-CSF at 20 ng/ml). Recombinant murine CXCL9 (rMuMig at 300 ng/ml) was added to the above culture to test its function; and equal volume of the vehicle phosphate buffered saline (PBS) was added to the duplicate cultures above as control.

After 4 hrs incubation of the cells, Ara-C was added to the culture at a final concentration of 1 mM. The cells were further incubated for 1 hr, and followed by washing the cells with PBS once. Third, the cells were further cultured for 4 hrs. Finally, Ara-C was added at 1 mM to the cells and incubated for 0.5 hr. The cells were washed by PBS twice, and resuspended in PBS at $10^5$/ml.

Syngeneic 8-week-old C57BL/6 male mice were used as recipient of the cultured cells. The mice were lethally irradiated by Cesium-137 ($^{137}$Cs) at the dose of 790 cGy. Four hrs after radiation the mice were injected with $10^4$ cultured cells at volume of 100 microliter through tail vein. The CXCL9 treated cells were injected into 13 mice; the PBS treated cells were injected into 8 mice.

Eleven (11) days after the cell transplantation, the recipient mice were sacrificed and their spleens were removed and fixed in formalin. The whitish colonies of the spleens were counted under dissecting microscope. The results of the CFU-S are shown in the Figure above for individual mouse. The Mean±SD of the rMuMig treated cells was 12.1±2.6, compared with the PBS treated cells 7.8±2.7, with the P<0.01 assessed by two tailed Student's t test.

The data demonstrate that pre-incubation of HSCs with CXCL9 reduces the killing of HSCs by Ara-C in vitro, indicating the protective roles of CXCL9 to the HSCs from the damage of chemotherapeutic agents. Taken together with our cell cycle analysis data which demonstrate CXCL9 reduces the cell cycle progression of hematopoietic cells strongly suggest that the observed protective role CXCL9 against Ara-C is mediated by suppression of cell cycle progression of HSCs. Increased expression of CXCL9 and its receptor CXCR3 in BM hematopoietic cells after chemotherapy causes delayed recovery of hematopoiesis. Hence, use of the CXCR3 antagonists should facilitate the recovery of BM function.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and compositions within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub ranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

All references cited herein are incorporated by reference in their entireties and for all purposes to the same extent as if each individual publication, patent, or patent application was specifically and individually incorporated by reference in its entirety for all purposes.

Other embodiments are set forth within the following claims.

What is claimed is:

1. A method for enhancing hematopoietic recovery following chemotherapy or radiotherapy, the method comprising:
administering to a subject after chemotherapy or radiotherapy an effective amount of a CXCR3 antagonist, wherein the CXCR3 antagonist is selected from the group consisting of: an anti-CXCL9 antibody, an anti-CXCL10 antibody, an anti-CXCL11 antibody, an anti-CXCR3 antibody, and combinations thereof, and following chemotherapy or radiotherapy the bone marrow cell density or the level of peripheral white blood cells of the subject is increased compared to a control subject not receiving the CXCR3 antagonist.

2. The method of claim 1, wherein the CXCR3 antagonist is administered in daily doses for two or more days following the administration of the chemotherapy or the radiotherapy.

3. The method of claim 1 further comprising administering a hematopoietic growth factor to the subject following the chemotherapy or the radiotherapy.

4. The method of claim 3, wherein the growth factor is one or more of GM-CSF, G-CSF, TPO, or IL-11.

5. The method of claim 1, wherein the CXCR3 antagonist is an anti-CXCL9 antibody.

* * * * *